(12) United States Patent  
Smith et al.

(10) Patent No.: US 9,089,375 B2  
(45) Date of Patent: Jul. 28, 2015

(54) COMBINED INTRAMEDULLARY AND EXTRAMEDULLARY SURGICAL AIMING SYSTEM AND METHOD

(71) Applicants: Joel Smith, San Diego, CA (US); Aaron Osborne, Redding, CA (US); Brian Chalkin, Tulsa, OK (US)

(72) Inventors: Joel Smith, San Diego, CA (US); Aaron Osborne, Redding, CA (US); Brian Chalkin, Tulsa, OK (US)

(73) Assignee: Interfix, LLC, Redding, CA (US)

( * ) Notice: Subject to any disclaimer, the term of this patent is extended or adjusted under 35 U.S.C. 154(b) by 0 days.

(21) Appl. No.: 14/306,683

(22) Filed: Jun. 17, 2014

(65) Prior Publication Data

US 2015/0105779 A1 Apr. 16, 2015

Related U.S. Application Data

(60) Provisional application No. 61/890,240, filed on Oct. 12, 2013, provisional application No. 61/934,692, filed on Jan. 31, 2014.

(51) Int. Cl.

| | | |
|---|---|---|
| *A61B 17/68* | (2006.01) | |
| *A61B 17/58* | (2006.01) | |
| *A61B 17/60* | (2006.01) | |
| *A61F 2/00* | (2006.01) | |
| *A61F 2/46* | (2006.01) | |
| *A61F 5/00* | (2006.01) | |
| *A61B 17/80* | (2006.01) | |
| *A61B 17/90* | (2006.01) | |

(52) U.S. Cl.  
CPC .............. *A61B 17/808* (2013.01); *A61B 17/80* (2013.01); *A61B 2017/90* (2013.01)

(58) Field of Classification Search  
USPC .......................... 606/86 R, 86 B, 87, 104, 915  
See application file for complete search history.

(56) References Cited

U.S. PATENT DOCUMENTS

| | | |
|---|---|---|
| 4,465,065 A | 8/1984 | Gotfried |
| 5,366,457 A | 11/1994 | McGuire et al. |
| 5,458,654 A | 10/1995 | Tepic |
| 5,658,283 A | 8/1997 | Huebner |
| 5,853,415 A | 12/1998 | Bertin et al. |
| 5,928,234 A | 7/1999 | Manspeizer |
| 6,514,253 B1 | 2/2003 | Yao |
| 6,527,775 B1 | 3/2003 | Warburton |
| 6,579,293 B1 | 6/2003 | Chandran |
| 6,692,496 B1 | 2/2004 | Wardlaw |
| 6,706,046 B2 | 3/2004 | Orbay et al. |
| 6,746,453 B2 | 6/2004 | Deloge et al. |
| 7,488,323 B2 | 2/2009 | Bacastow et al. |
| 7,588,577 B2 | 9/2009 | Fencl et al. |
| 7,621,920 B2 | 11/2009 | Claypool et al. |

(Continued)

*Primary Examiner* — Sameh Boles  
(74) *Attorney, Agent, or Firm* — Shannon L Warren

(57) ABSTRACT

A surgical aiming system is disclosed comprising a one or more fixation plates, an aiming assembly, a one or more nails and a plurality of screws. Said aiming assembly comprising a channeling assembly and a plurality of channels. Said one or more fixation plates comprising a plurality of plate apertures capable of receiving a portion of said plurality of screws. Said plurality of channels in said aiming assembly are capable of aligning a portion of said plurality of screws with said plurality of plate apertures in a first fixation plate. Said plurality of channels receive and align said plurality of screws as they are secured to said first bone. Said first fixation plate being extramedullary attached to a portion of said surface of said first bone; and said plurality of channels of said aiming assembly being aligned to identify a one or more intramedullary locations within said first bone.

9 Claims, 27 Drawing Sheets

(56) References Cited

U.S. PATENT DOCUMENTS

| | | |
|---|---|---|
| 7,648,508 B2 | 1/2010 | Lutz et al. |
| 7,686,808 B2 | 3/2010 | Orbay et al. |
| 7,727,236 B2 | 6/2010 | Choe et al. |
| 7,771,441 B2 | 8/2010 | Cerundolo |
| 7,833,230 B2 | 11/2010 | Cerundolo |
| 7,837,689 B2 | 11/2010 | Leyden et al. |
| 8,034,056 B2 | 10/2011 | Fencl et al. |
| 8,114,093 B2 | 2/2012 | Matthys |
| 8,142,432 B2 | 3/2012 | Matityahu |
| 8,162,950 B2 | 4/2012 | Digeser et al. |
| 8,282,638 B2 | 10/2012 | Choe et al. |
| 8,439,932 B2 | 5/2013 | Sheffer |
| 8,679,130 B2 * | 3/2014 | Smith et al. .................... 606/96 |
| 2003/0055428 A1 | 3/2003 | Swanson |
| 2003/0216742 A1 | 11/2003 | Wetzler et al. |
| 2011/0106086 A1 | 5/2011 | Laird |

\* cited by examiner

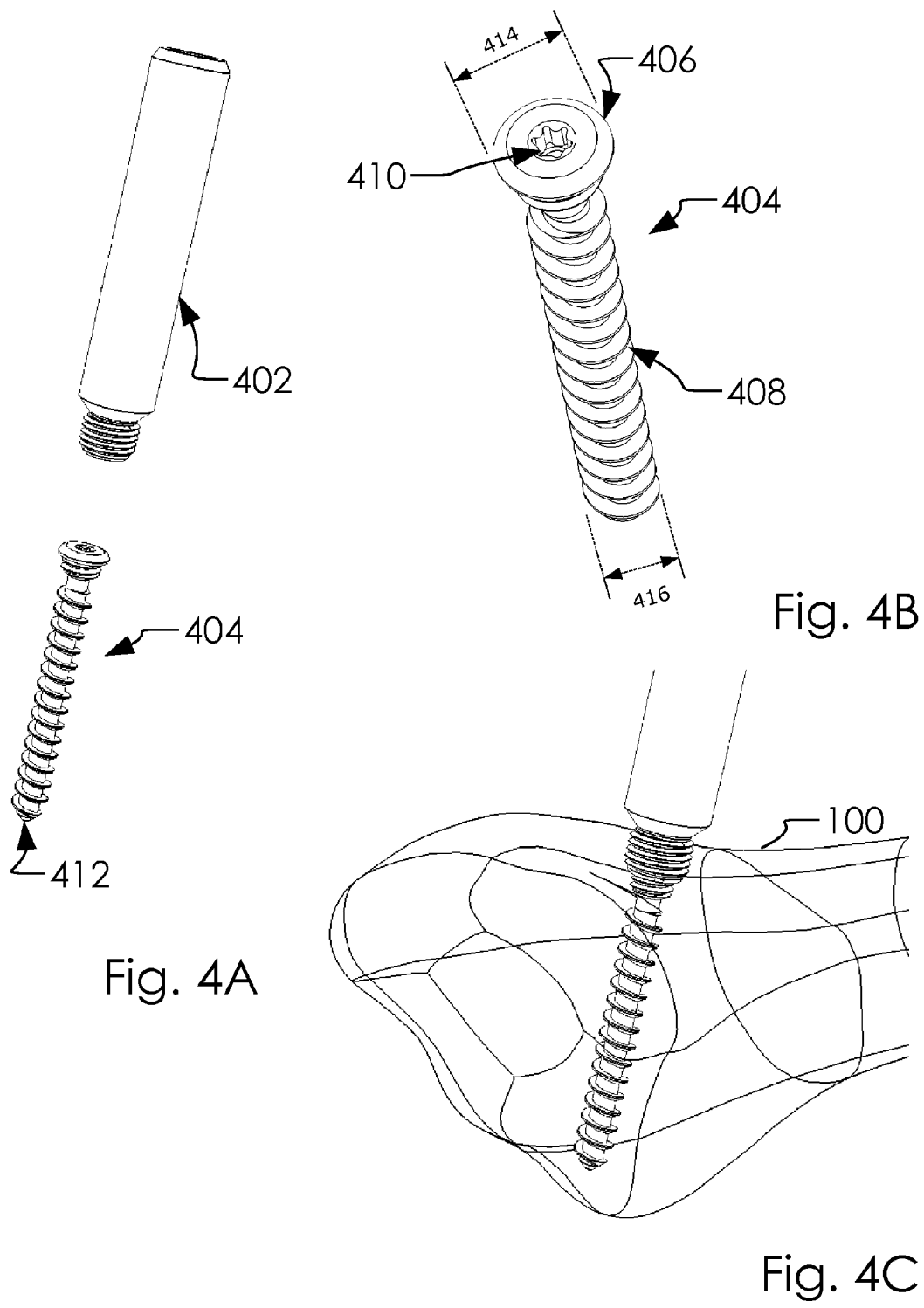

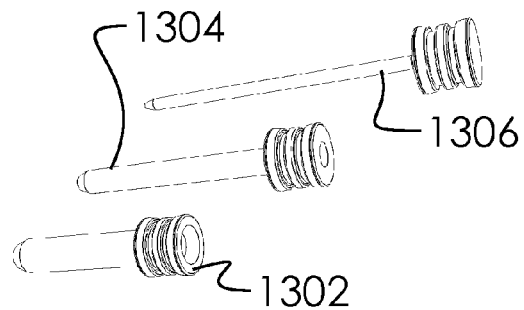
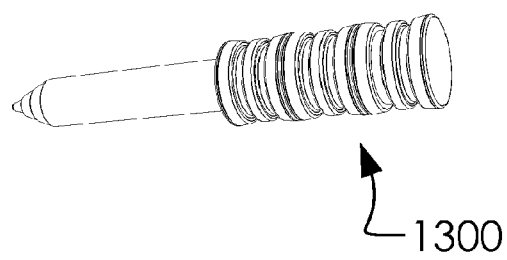
Fig. 13A　　　　　　　　Fig. 13B
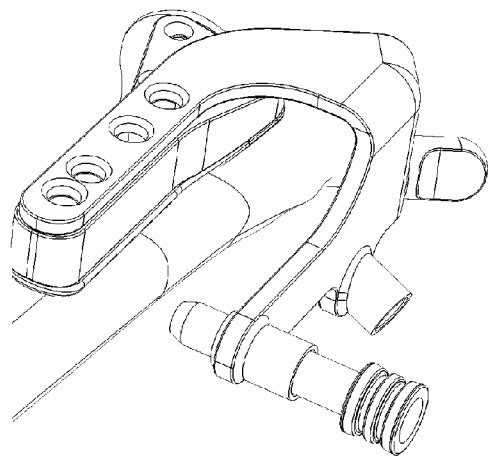
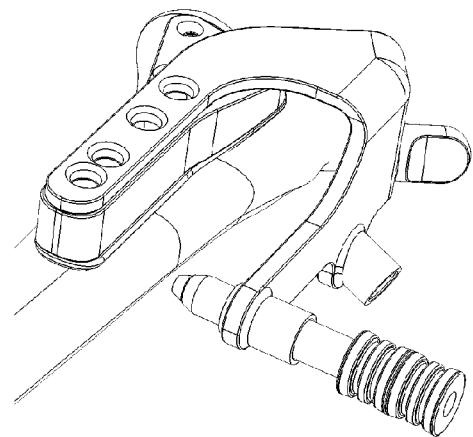
Fig. 13C　　　　　　　　Fig. 13D
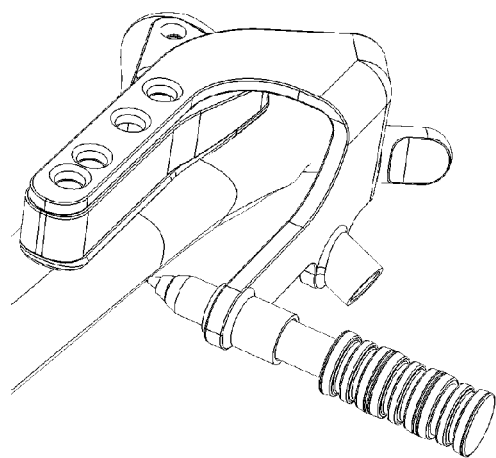
Fig. 13E

COMBINED INTRAMEDULLARY AND EXTRAMEDULLARY SURGICAL AIMING SYSTEM AND METHOD

CROSS-REFERENCE TO RELATED APPLICATIONS

This application is the nonprovisional filing made on the basis of U.S. Provisional Patent Application Nos. 61/890,240 (filed on Oct. 12, 2013), and 61/934,692 (filed Jan. 31, 2014).

STATEMENT REGARDING FEDERALLY SPONSORED RESEARCH OR DEVELOPMENT (IF APPLICABLE)

Not applicable.

REFERENCE TO SEQUENCE LISTING, A TABLE, OR A COMPUTER PROGRAM LISTING COMPACT DISC APPENDIX (IF APPLICABLE)

Not applicable.

BACKGROUND OF THE INVENTION

This disclosure relates generally to a surgical aiming system and method. Surgical systems for aiming plates and screws are well-known and include products by companies such as Synthes®, Zimmer®, Stryker®, and Biomet®. A few examples of surgical systems includes: U.S. Pat. No. 4,465,065A, US20110224736A1, U.S. Pat. No. 8,523,862B2, U.S. Pat. No. 8,523,919B2, U.S. Pat. No. 6,926,720B2, US20090228047A1, U.S. Pat. No. 8,556,945B2, U.S. Pat. No. 8,545,540B2, U.S. Pat. No. 6,342,057B1, U.S. Pat. No. 4,465,065, U.S. Pat. No. 5,366,457, U.S. Pat. No. 5,458,654, U.S. Pat. No. 5,658,283, U.S. Pat. No. 5,853,415, U.S. Pat. No. 5,928,234, U.S. Pat. No. 6,514,253, U.S. Pat. No. 6,527,775, U.S. Pat. No. 6,579,293, U.S. Pat. No. 6,692,496, U.S. Pat. No. 6,706,046, U.S. Pat. No. 6,746,453, US20030055428, US20030216742, U.S. Pat. No. 7,488,323, U.S. Pat. No. 7,588,577, U.S. Pat. No. 7,621,920, U.S. Pat. No. 7,648,508, U.S. Pat. No. 7,686,808, U.S. Pat. No. 7,727,236, U.S. Pat. No. 7,771,441, U.S. Pat. No. 7,833,230, U.S. Pat. No. 7,837,689, U.S. Pat. No. 8,034,056, U.S. Pat. No. 8,114,093, U.S. Pat. No. 8,142,432, U.S. Pat. No. 8,162,950, U.S. Pat. No. 8,282,638, U.S. Pat. No. 8,439,932, US20110106086, WO2007086854A1, WO2007109437A2, WO2008098016A2, and WO2009121144A1. However, none of the prior inventions and/or patents, taken either singularly or in combination, is seen to describe the instant disclosure as claimed.

Accordingly, an improved surgical aiming system and method would be advantageous.

BRIEF SUMMARY OF THE INVENTION

A surgical aiming system is disclosed comprising a one or more fixation plates, an aiming assembly, a one or more nails and a plurality of screws. Said one or more fixation plates comprising a first fixation plate. Said aiming assembly comprising a channeling assembly and a plurality of channels. Said one or more fixation plates comprising a plurality of plate apertures capable of receiving a portion of said plurality of screws. Said plurality of channels in said aiming assembly are capable of aligning a portion of said plurality of screws with said plurality of plate apertures in said first fixation plate. Said first fixation plate having a first end, a second end, a top surface, and a bottom surface. Said plurality of plate apertures comprising a first plate aperture and a second first plate aperture. Said channeling assembly having a thickness, a top surface, and a bottom surface. Said bottom surface of said first fixation plate substantially couples with a surface of a first bone of a skeletal system. Said bottom surface said aiming assembly substantially couples with said top surface of said first fixation plate. Said plurality of channels receive and align said plurality of screws as said plurality of screws are inserted through said plurality of plate apertures and secured to said first bone. Said first fixation plate being extramedullary attached to a portion of said surface of said first bone; and said plurality of channels of said aiming assembly being aligned to identify a one or more intramedullary locations including an entry point for said one or more nails, and an alignment and entry point for each among said plurality of plate apertures.

BRIEF DESCRIPTION OF THE SEVERAL VIEWS OF THE DRAWING

FIGS. 4A, 4B and 4C illustrate a perspective overview of a drill guide with a screw, with said drill guide, and said screw inserted into a wireframe view of said first bone.

FIG. 5A illustrates said first bone as a solid view and 5B illustrates said first bone in a wireframe view.

FIGS. 13A, 13B, 13C, 13D and 13E illustrate a series of perspective overviews of a stacked drilling system.

DETAILED DESCRIPTION OF THE INVENTION

Described herein is a combined intramedullary and extramedullary surgical aiming system and method. The following description is presented to enable any person skilled in the art to make and use the invention as claimed and is provided in the context of the particular examples discussed below, variations of which will be readily apparent to those skilled in the art. In the interest of clarity, not all features of an actual implementation are described in this specification. It will be appreciated that in the development of any such actual implementation (as in any development project), design decisions must be made to achieve the designers' specific goals (e.g., compliance with system- and business-related constraints), and that these goals will vary from one implementation to another. It will also be appreciated that such development effort might be complex and time-consuming, but would nevertheless be a routine undertaking for those of ordinary skill in the field of the appropriate art having the benefit of this disclosure. Accordingly, the claims appended hereto are not intended to be limited by the disclosed embodiments, but are to be accorded their widest scope consistent with the principles and features disclosed herein.

Figure 1A:
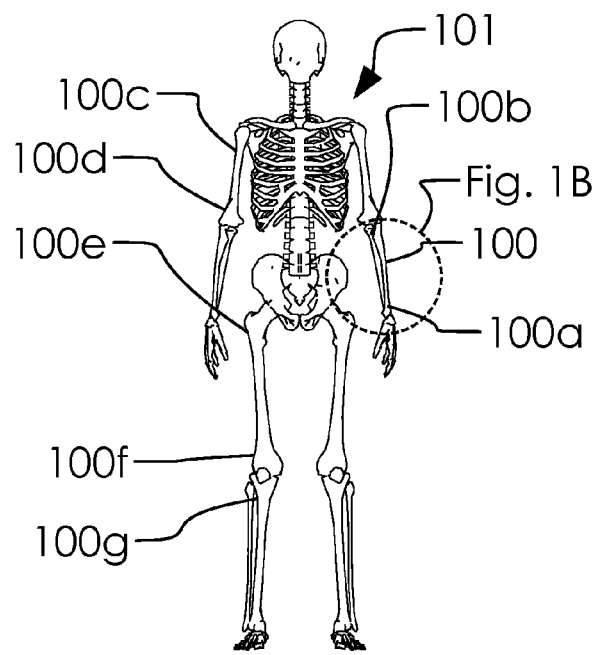
FIGS. 1A and 1B illustrate an elevated front view of a skeletal system and a perspective anterior view of a first bone with a first fixation plate.
Figure 1B:
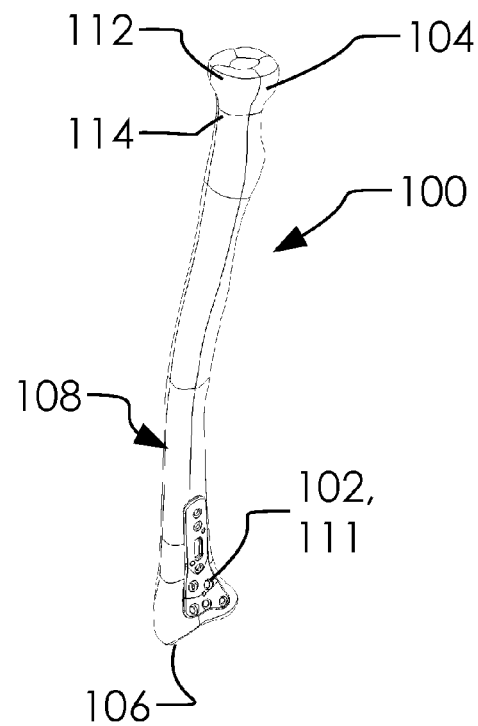

FIGS. 1A and 1B illustrate an elevated front view of a skeletal system 101 and a perspective anterior view of a first bone 100 with a first fixation plate 102. In one embodiment, said first fixation plate 102 can comprise a portion of a surgical aiming system 111 as illustrated more fully below. In one embodiment, said surgical aiming system 111 can comprise one or more components and methods of using said one or more components. In one embodiment, said surgical aiming system 111 can be used to treat fractures of long bones (such as first bone 100) of said skeletal system 101. In one embodiment, said first bone 100 can comprise a radius bone of said skeletal system 101. Although said skeletal system 101 comprises a human skeletal system, said surgical aiming system 111 can be used on other skeletal systems, such as non-human mammals. For illustrative purposes, said first bone 100 is used in this disclosure, but this use should not be construed as limiting to one among many bones within said skeletal system 101 which may be benefited by the current disclosure. For example, said surgical aiming system 111 can be used on a distal radius 100a, a proximal ulna 100b, a proximal humerus 100c, a distal humerus 100d, a proximal femur 100e, a distal femur 100f, a proximal tibia 100g, or similar as is known in the art.

First bone 100 can comprise a first end 104 (or the proximal radius), a second end 106 (or the distal radius) and a surface 108. First end 104 can comprise a portion of first bone 100 comprising a radial head 112 and a neck 114. Second end 106 can comprise a portion of first bone 100 comprising a syloid process, a baze-carpal articular surface and an ulnar noch, as is known in the art. In one embodiment, said first fixation plate 102 can attach to said surface 108 of said second end 106 of said first bone 100, or in this case the distal radius.

Figure 2A:
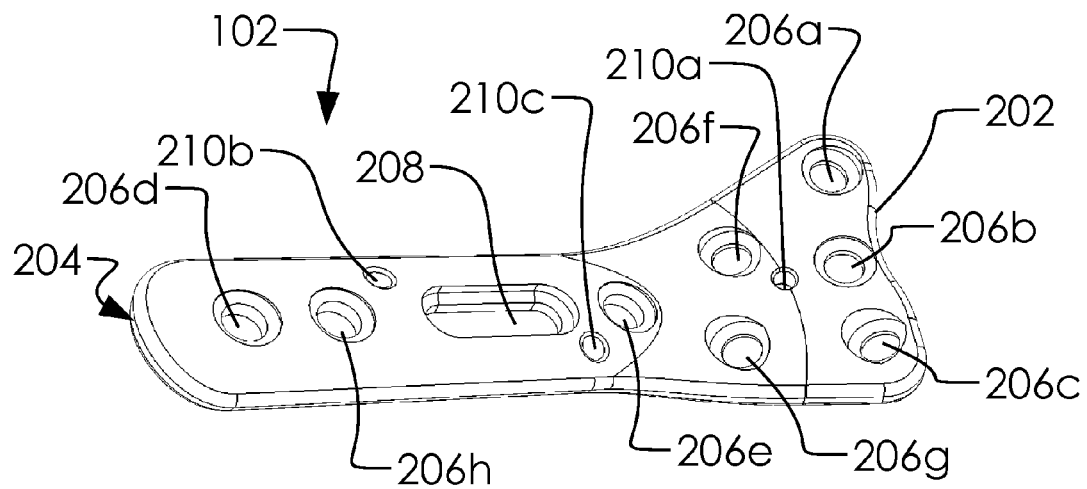
FIGS. 2A, 2B and 2C illustrate a perspective overview, an elevated bottom view and an elevated side view of said first fixation plate.
Figure 2B:
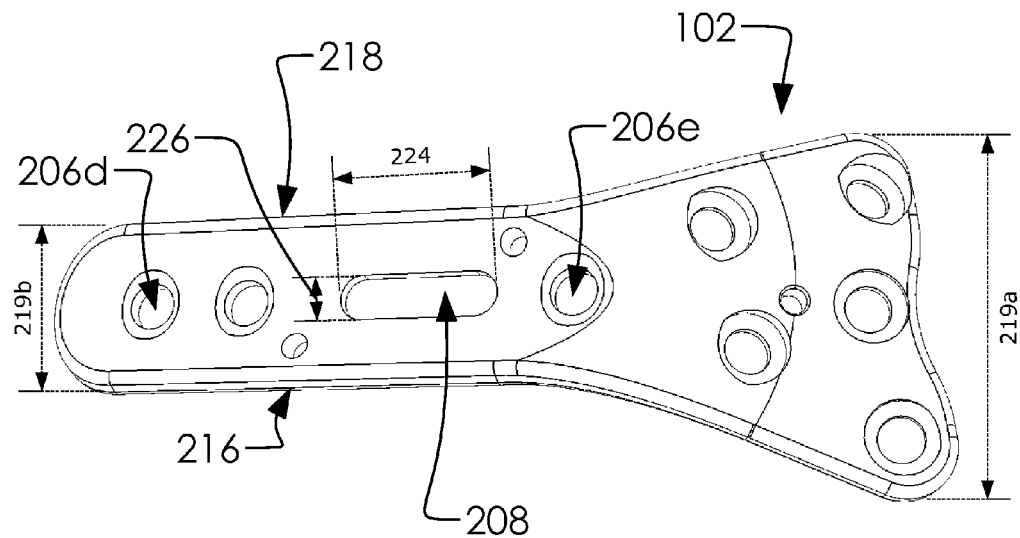
Figure 2C:
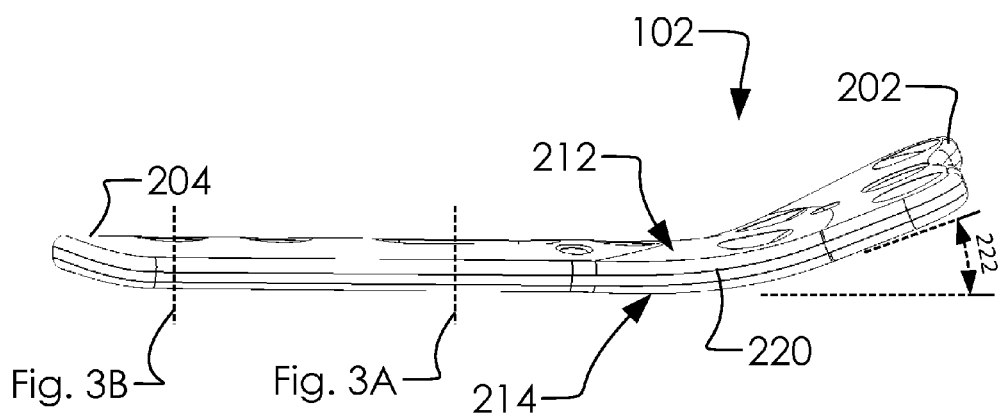

FIGS. 2A, 2B and 2C illustrate a perspective overview, an elevated bottom view and an elevated side view of said first fixation plate 102. In one embodiment, said surgical aiming system 111 can comprise a one or more fixation plates (comprising said first fixation plate 102). Said first fixation plate 102 can comprise a first end 202 and a second end 204. In one embodiment, said first fixation plate 102 can comprise an elongated planar object comprising a substantially smooth surface and rounded edges, adapted to couple with said surface 108 of said first bone 100. In one embodiment, said first end 202 can be broader than said second end 204.

In one embodiment, said first fixation plate 102 can comprise a plurality of plate apertures. In one embodiment, said plurality of plate apertures can each receive a portion of a surgical screw or other binding tool (as discussed infra). In one embodiment, said plurality of plate apertures can comprise a first plate aperture 206a, a second plate aperture 206b, a third plate aperture 206c, a fourth plate aperture 206d, a fifth plate aperture 206e, a sixth plate aperture 206f, a seventh plate aperture 206g, an eighth plate aperture 206h, a central plate aperture 208, a first wire aperture 210a, a second wire 210b, and a third wire aperture 210c.

First fixation plate 102 can comprise a top surface 212, a bottom surface 214, a first side 216 and a second side 218. In one embodiment, said first end 202 can comprise a width 219a and said second end 204 can comprise a width 219b. In one embodiment, said width 219a can be wider than said width 219b. In one embodiment, said first fixation plate 102 can comprise a substantially planar shape with portions of said bottom surface 214 shaped to couple (or mate) with said surface 108 of said first bone 100. Thus, in one embodiment said first fixation plate 102 can comprise a bend 220 between said first end 202 and said second end 204. In one embodiment, as seen from an elevated view of said second side 218, said second end 204 can comprise a substantially straight portion of said first fixation plate 102, followed by said bend 220, and said second side 218 at said first end 202 can be bent up by a bend angle 222, as illustrated.

In one embodiment, some of said plurality of plate apertures (such as first plate aperture 206a, second plate aperture 206b, third plate aperture 206c and fourth plate aperture 206d) can comprise a substantially circular shape. In one embodiment, however, central plate aperture 208 can comprise a substantially elliptical shape comprising a length 224 being longer than a width 226.

Cross-section cut lines are illustrated in FIG. 2C for FIGS. 3A and 3B, as discussed below.

Figure 3A:
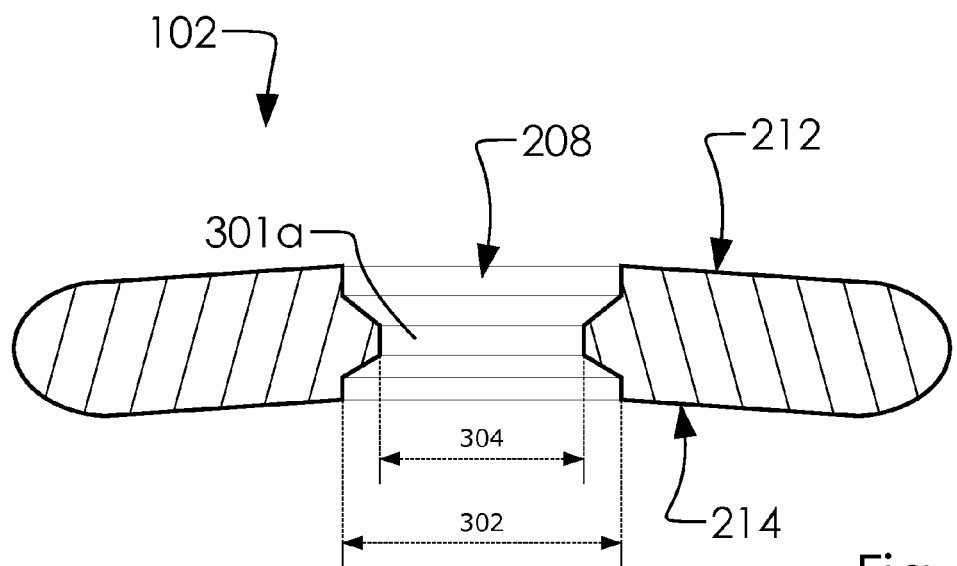
FIGS. 3A and 3B illustrate an elevated cross-section view of said central plate aperture and said fourth plate aperture, respectively.
Figure 3B:
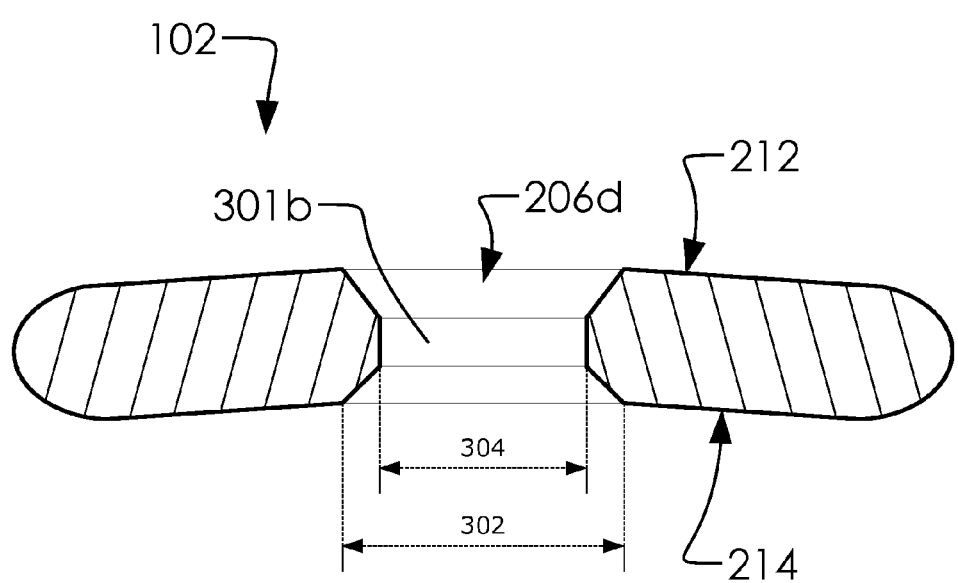

FIGS. 3A and 3B illustrate an elevated cross-section view of said central plate aperture 208 and said fourth plate aperture 206d, respectively. In one embodiment, said top surface 212 can be substantially convex. In one embodiment, said bottom surface 214 can be substantially concave. In one embodiment, bottom surface 214, being substantially concave, can press against and couple with said surface 108 of said second end 106 of said first bone 100 (being substantially convex). Thus, in one embodiment said first fixation plate 102 can couple with said surface 108 of said first bone 100.

In one embodiment, each among said plurality of plate apertures can comprise an inner lip; e.g., said central plate aperture 208 can comprise a first inner lip 301a and said fourth plate aperture 206d can comprise a second inner lip 301b. In one embodiment, said fourth plate aperture 206d and said central plate aperture 208 can each comprise a first diameter 302. In one embodiment, said first inner lip 301a—being substantially elliptical—can comprise a second diameter 304. However, said central plate aperture 208 and said fourth plate aperture 206d may have different diameters in another embodiment. In one embodiment, said second diameter 304 is wide enough to accommodate a shaft and threading of a screw but narrow enough to catch a head of said screw, as discussed infra, and as is known in the art.

FIGS. 4A, 4B and 4C illustrate a perspective overview of a drill guide 402 with a screw 404, with said drill guide 402, and said screw 404 inserted into a wireframe view of said first bone 100. Said screw 404 can comprise one of a range of well-known surgical screws, pegs, and/or locking or nonlocking implements; wherein, said screw 404 is capable of penetrating and holding a bone (such as first bone 100). In one embodiment, said screw 404 can comprise a head 406 and a threaded portion 408, as is known in the art. In one embodiment, said head 406 can comprise a fitting portion 410. In one embodiment, a portion of said drill guide 402 can attach to said fitting portion 410 and drive said screw 404 in a rotary and linear direction, as is well-known in the art. In one embodiment, said drill guide 402 can be used to guide a drill bit in establishing a pathway prior to affixing a one or more screws. In one embodiment, said screw 404 can comprise a tip 412. In one embodiment, said tip 412 can be sharpened and capable of penetrating first bone 100. In one embodiment, as is known in the art, screwing said screw 404 into said first bone 100 can comprise: aligning said tip 412 on said first bone 100, rotating said screw 404, and pressing said screw 404 into said first bone 100 to a desired depth.

Head 406 can comprise an external diameter 414. Threaded portion 408 can comprise an external diameter 416. In one embodiment, said external diameter 414 is greater than second diameter 304 of said plurality of plate apertures. In one embodiment, said external diameter 416 is smaller than said second diameter 304 of said plurality of plate apertures. Thus, said plurality of plate apertures are capable of allowing a portion of said screw 404 to penetrate said first fixation plate 102 while holding a portion of said first fixation plate 102 against said surface 108 with said head 406 of said screw 404.

Figure 5A:
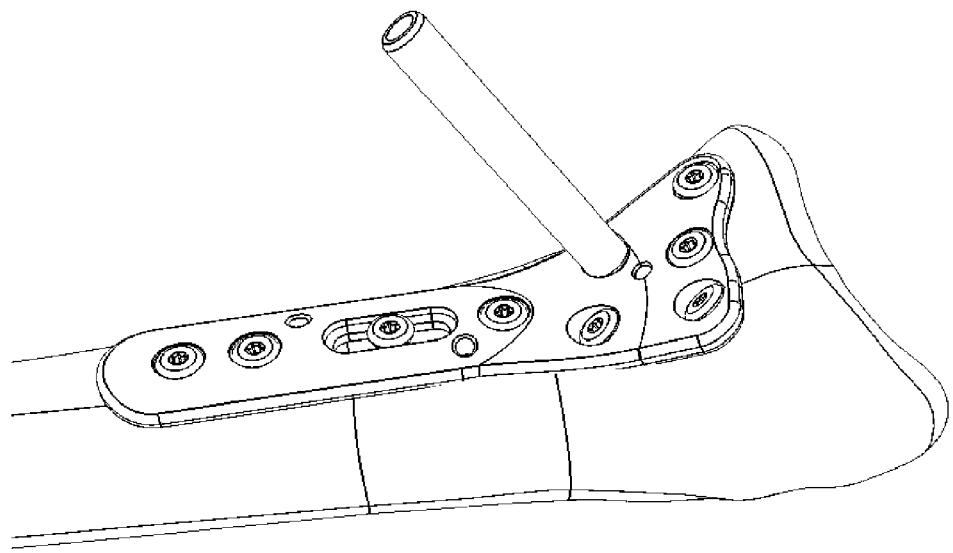
FIGS. 5A and 5B illustrate a perspective overview of said first fixation plate attached to said first bone with a plurality of screws.
Figure 5B:
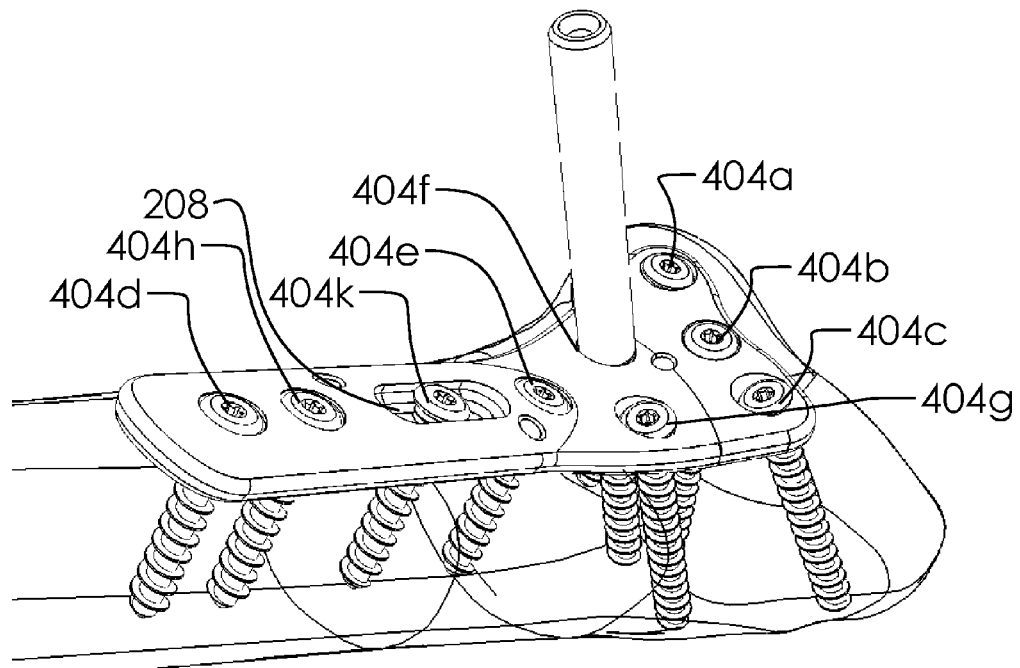

FIGS. 5A and 5B illustrate a perspective overview of said first fixation plate 102 attached to said first bone 100 with a plurality of screws. FIG. 5A illustrates said first bone 100 as a solid view and 5B illustrates said first bone 100 in a wireframe view. In one embodiment, said plurality of screws can comprise a plurality of said screw 404. In one embodiment, attaching said first fixation plate 102 to said first bone 100 can comprise: aligning said first fixation plate 102 with said second end 106 of said first bone 100, and screwing said plurality of screws into said plurality of plate apertures of said first fixation plate 102. In one embodiment, said bottom surface 214 of said first fixation plate 102 can be substantially flat against said surface 108 of said first bone 100 prior to attaching said first fixation plate 102 to said first bone 100.

Note here that said plurality of screws are inserted into said first bone 100 at a, seemingly, random set of angles relative to one another. However, the positioning, angles and depth of said plurality of screws are the result of careful thought and preparation by surgeons. Consequently, as follows, said surgical aiming system 111 can be used to insert said plurality of screws at predetermined locations and angles relative to other components of said surgical aiming system 111.

In one embodiment, said plurality of screws can comprise a first screw 404a, a second screw 404b, a third screw 404c, a fourth screw 404d, a fifth screw 404e, a sixth screw 404f, a seventh screw 404g, an eighth screw 404h, and said ninth screw 404k.

Figure 5C:
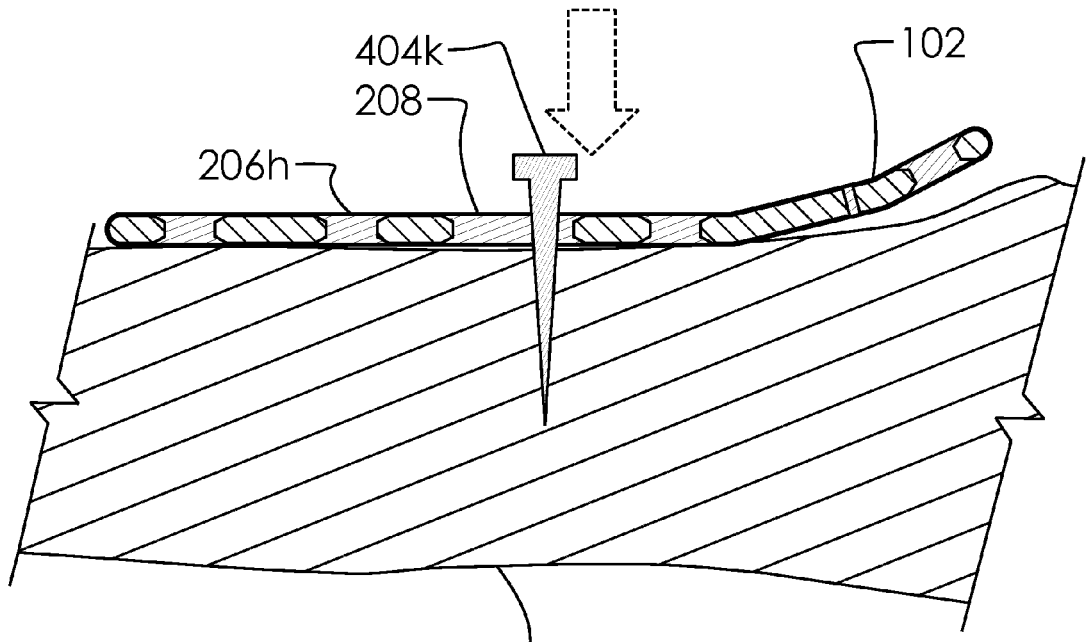
FIGS. 5C and 5D illustrate a cross-section elevated front view of said first fixation plate and said first bone.
Figure 5D:
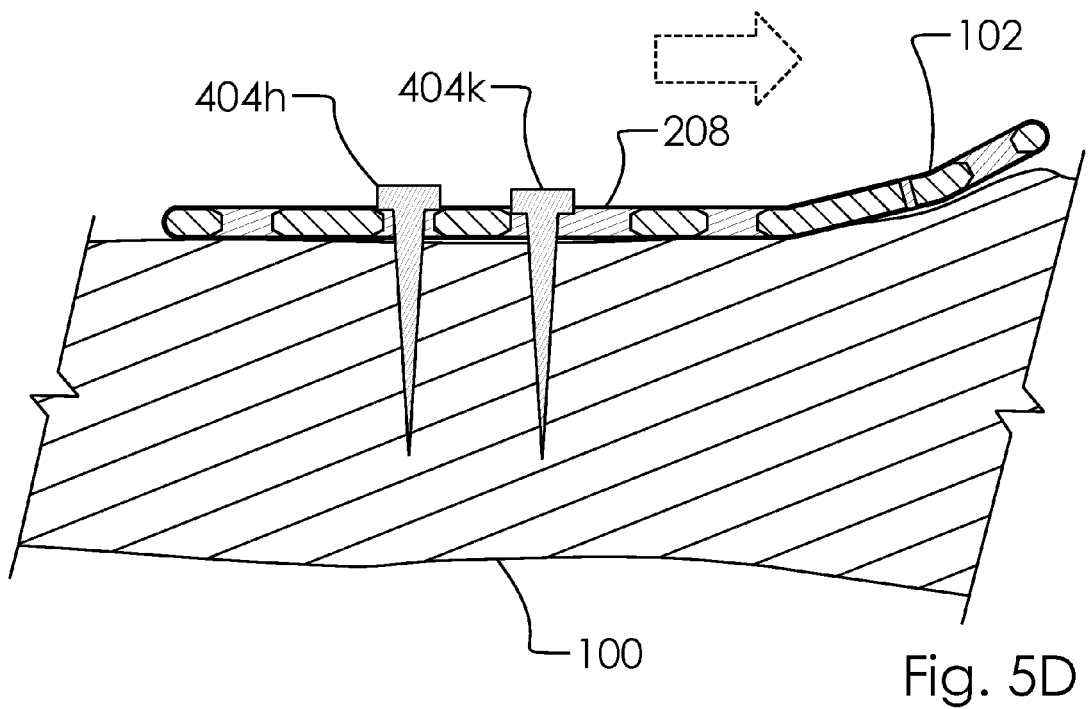

FIGS. 5C and 5D illustrate a cross-section elevated front view of said first fixation plate 102 and said first bone 100. In one embodiment, screwing said plurality of screws into said plurality of plate apertures can comprise: screwing said ninth screw 404k through said central plate aperture 208 (see FIG. 5C); sliding said first fixation plate 102 toward said second end 106 along said length 224 of said central plate aperture 208 to a final position; tightening said ninth screw 404k; holding said first fixation plate 102 against said first bone 100 with said ninth screw 404k; and screwing a one or more of said plurality of screws into said plurality of plate apertures (such as said eighth screw 404h through said eighth plate aperture 206h, as illustrated in FIG. 5D). Note that said plurality of screws are illustrated in FIGS. 5C and 5D without threading, but this is done for clarity of positioning and should not be construed of a selection of a preferred implement for attaching and holding said first fixation plate 102 to said first bone 100. In a preferred embodiment said plurality of plate apertures have threading, as is known in the art.

Figure 6A:
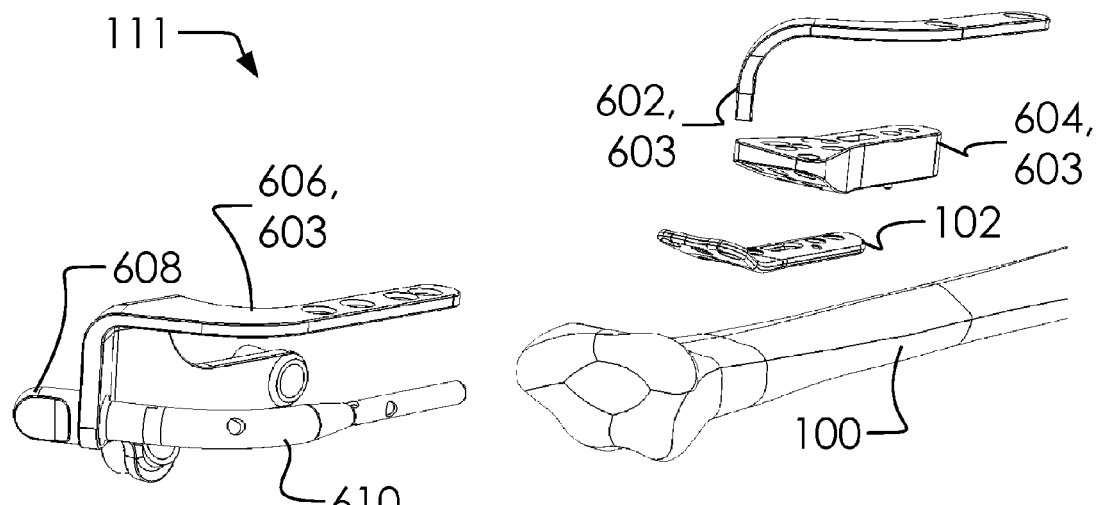
FIGS. 6A and 6B illustrate an exploded perspective first side overview and second side overview of said surgical aiming system with said first bone.
Figure 6B:
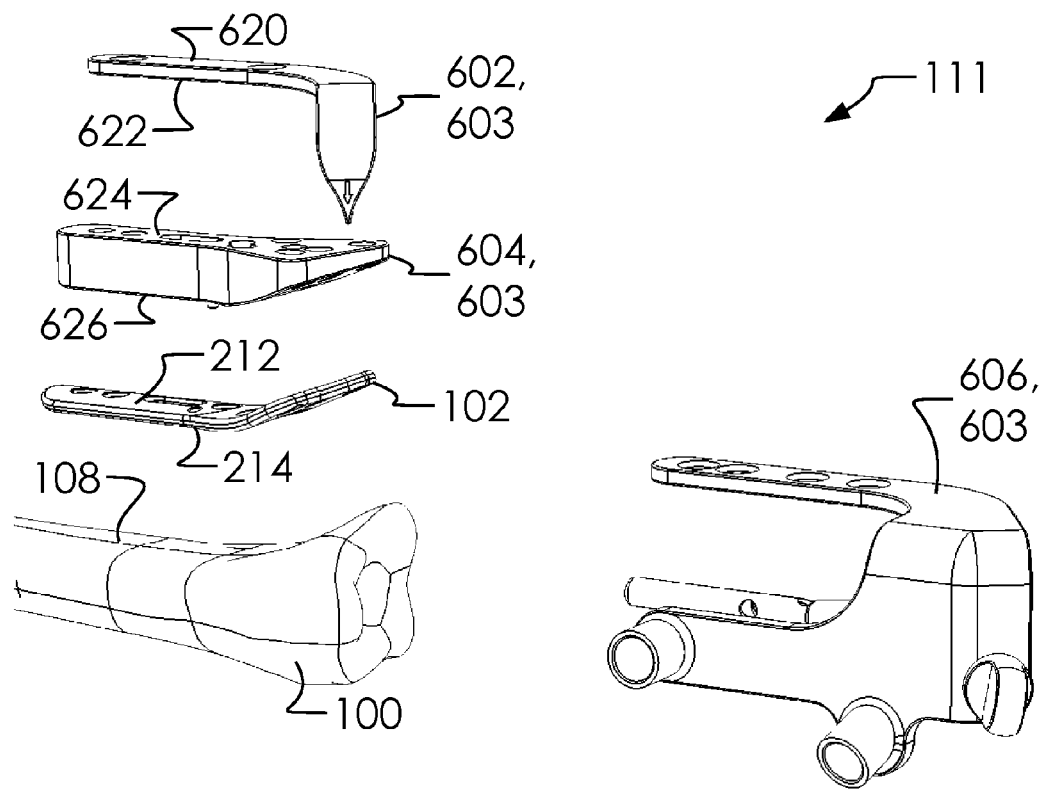

FIGS. 6A and 6B illustrate an exploded perspective first side overview and second side overview of said surgical aiming system 111 with said first bone 100. In one embodiment, said surgical aiming system 111 can comprise of an aiming assembly 603 (comprising of an intramedullary entry locator 602, a channeling assembly 604, a triangular screw guide 606, and a thumb screw 608), said first fixation plate 102, and a first nail 610. In one embodiment, said aiming assembly 603 can comprise of four independent parts or fewer parts, as will be discussed infra).

In one embodiment, said first nail 610 can comprise an intramedullary rod ("IM rod"), an intramedullary nail ("IM nail"), an inter-locking nail, or a Küntscher nail. In one embodiment, said first nail 610 can comprise a metal rod forced into the medullary cavity of a bone (such as first bone 100). intramedullary nails, like said first nail 610, have long been used to treat fractures of long bones of the body, as is well-known in the art.

In one embodiment, each among a one or more components of said surgical aiming system 111 can comprise a plurality of channels which, when held in alignment, are capable of precisely positioning said plurality of screws and said first nail 610 when inserted into said first bone 100. Thus, in one embodiment, said one or more components of said surgical aiming system 111 can be used to align and hold said first nail 610, as is discussed and illustrated infra.

In one embodiment, said aiming assembly 603 can comprise parts which break apart and are useful for different purposes while a surgeon is attaching said surgical aiming system 111 to said first bone 100. For example, said intramedullary entry locator 602 and said triangular screw guide 606 may not be used simultaneously, but in sequence, as discussed infra.

Focusing on FIG. 6B, in one embodiment, said intramedullary entry locator 602 can comprise a top surface 620 and a bottom surface 622. Likewise, in one embodiment, said channeling assembly 604 can comprise a top surface 624 and a bottom surface 626. In one embodiment, said bottom surface 622 of said intramedullary entry locator 602 mates with said top surface 624 of said channeling assembly 604; said bottom surface 626 of said channeling assembly 604 mates with said top surface 212 of said first fixation plate 102; and said bottom surface 214 of said first fixation plate 102 mates with said surface 108 of said first bone 100. In one embodiment, the term "mates" means that two components substantially abut one another having a geometry formed to securely stack against one another.

Figure 7A:
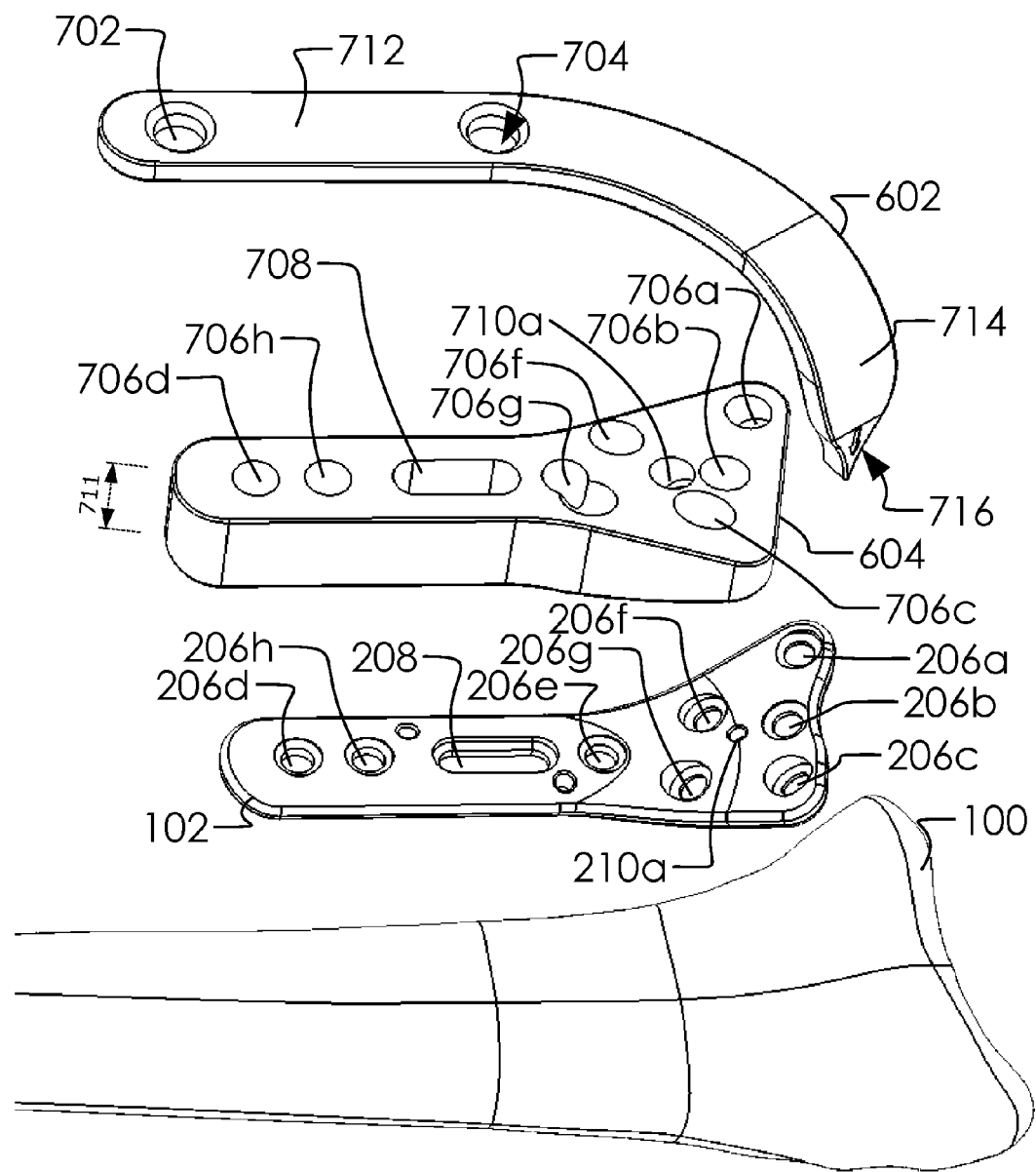
FIGS. 7A, 7B and 7C illustrate two exploded views and an attached perspective overview of said intramedullary entry locator, said channeling assembly, said first fixation plate and said first bone.
Figure 7B:
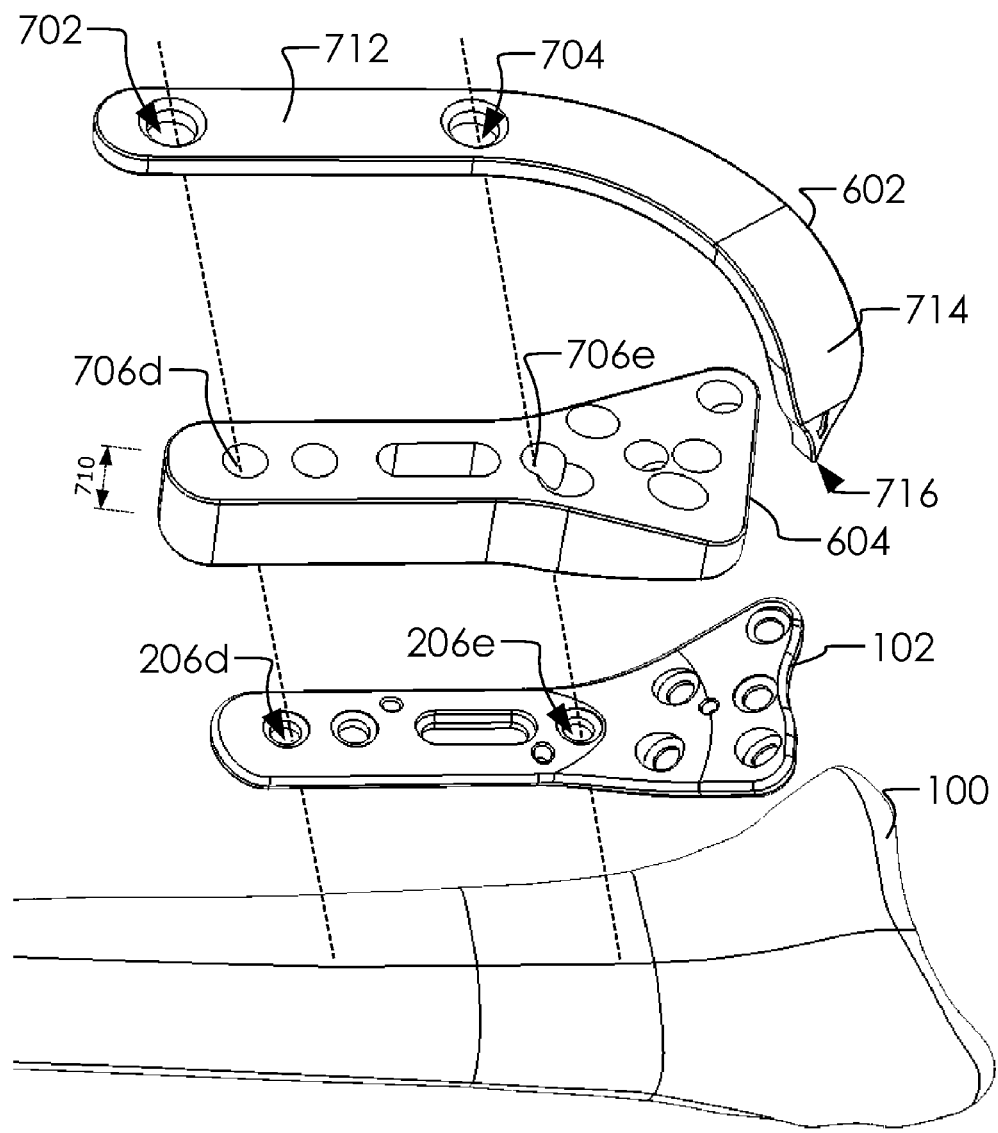
Figure 7C:
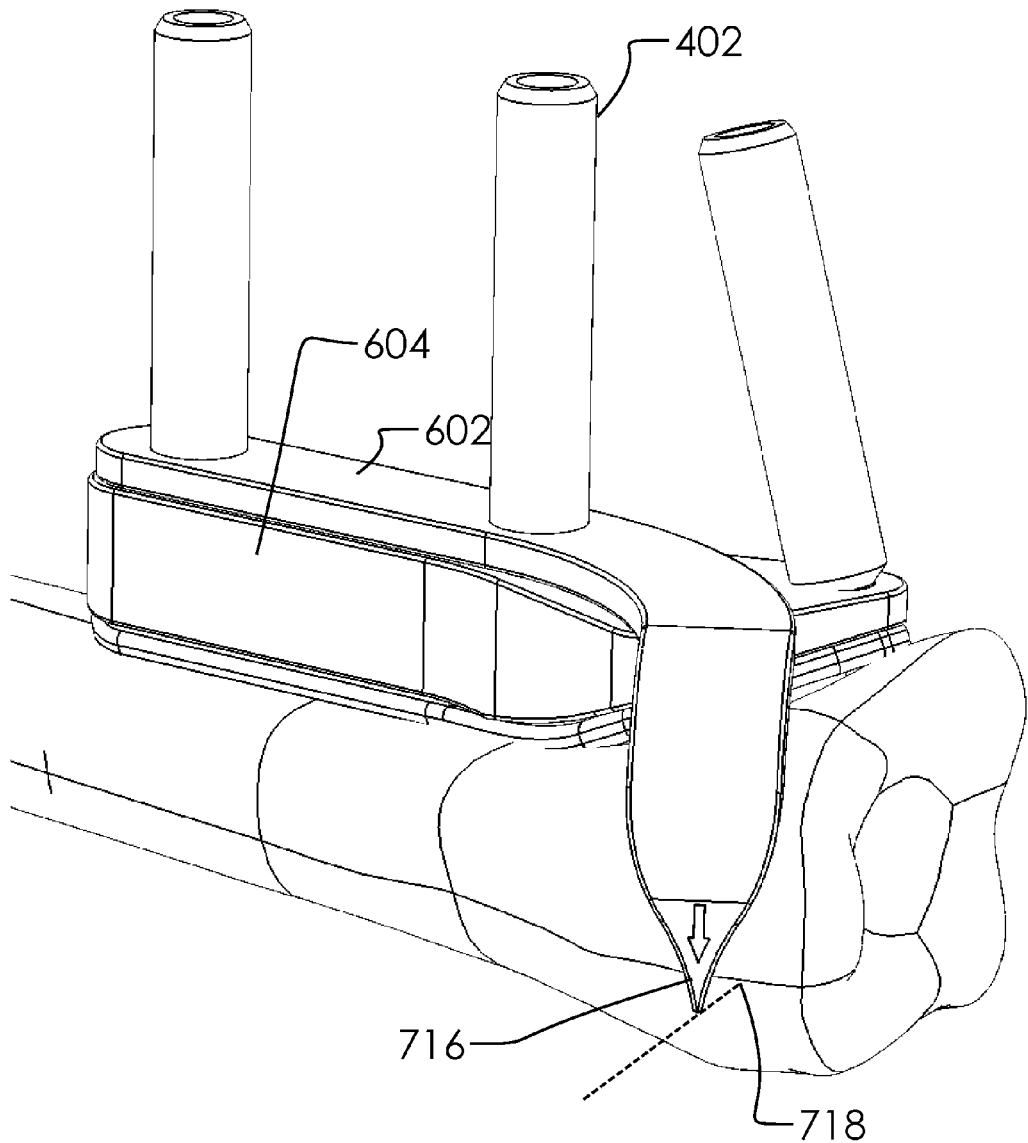

FIGS. 7A, 7B and 7C illustrate two exploded views and an attached perspective overview of said intramedullary entry locator 602, said channeling assembly 604, said first fixation plate 102 and said first bone 100.

In one embodiment, said aiming assembly 603 (here, said channeling assembly 604) can comprise a first channel 706a, a second channel 706b, a third channel 706c, a fourth channel 706d, a fifth channel 706e, a sixth channel 706f, a seventh channel 706g, an eighth channel 706h, a central channel 708, an first wire aperture 710a. Likewise, in one embodiment, said intramedullary entry locator 602 can comprise a first channel 702 and a second channel 704. In one embodiment, channeling assembly 604 can comprise a thickness 711.

In one embodiment, a method of using said surgical aiming system 111 can comprise: placing said first fixation plate 102 on a portion of said first bone 100; stacking said channeling assembly 604 on said first fixation plate 102, and said intramedullary entry locator 602 on top of said channeling assembly 604; aligning a portion of said plurality of channels in said intramedullary entry locator 602 with said channeling assembly 604 and said first fixation plate 102; guiding said plurality of screws through said plurality of channels; and attaching said plurality of screws to said first bone 100 at predetermined positions and angles. In one embodiment, said method of using said surgical aiming system 111 can further comprise: attaching said triangular screw guide 606 to said channeling assembly 604; inserting said first nail 610 into said first bone 100; and attaching said first nail 610 on a portion of said triangular screw guide 606.

In one embodiment, as illustrated in FIG. 7B, aligning and securing said intramedullary entry locator 602, said channeling assembly 604 and said first fixation plate 102 can comprise: aligning said first aperture 702 with said fourth channel 706d and said fourth plate aperture 206d; aligning said second aperture 704 with said fifth channel 706e and said fifth plate aperture 206e; inserting said fourth screw 404d through said first channel 702, said fourth channel 706d and said fourth plate aperture 206d; inserting said fifth screw 404e through said second channel 704, said fifth channel 706e and said fifth plate aperture 206e; and securing said fourth screw 404d and said fifth screw 404e to said first bone 100.

Prior to attaching said intramedullary entry locator 602 and said channeling assembly 604 to said first fixation plate 102, a portion of said first fixation plate 102 can be attached to said first bone 100.

In one embodiment, aligning said surgical aiming system 111 can further comprise: attaching said intramedullary entry locator 602 to said channeling assembly 604; and marking an entry point 718 with a pointing device 716 of said intramedullary entry locator 602; wherein, said entry point 718 can comprise an aligned location for inserting said first nail 610. In one embodiment, as illustrated in FIG. 7C, said intramedullary entry locator 602 can be held in alignment with said channeling assembly 604 by inserting one or more of said drill guide 402 through threaded portions of said first aperture 702 and/or said second aperture 704.

Said intramedullary entry locator 602 can comprise an upper portion 712 and a lower portion 714. In one embodiment, said upper portion 712 can comprise a substantially planar and horizontal member and said lower portion 714 can comprise a substantially vertical member of said intramedullary entry locator 602. In one embodiment, viewing said intramedullary entry locator 602 from an elevated side view, said upper portion 712 can be substantially horizontal, then gradually bend downward until lower portion 714 is substantially vertical. In one embodiment, lower portion 714 can comprise said pointing device 716. In one embodiment, said pointing device 716 can comprise marker for said entry point 718 for said first nail 610, as discussed infra.

In one embodiment, said one or more plates can hold a portion of said first bone from a plurality of surface locations around one or more nails within said first bone.

Figure 8A:
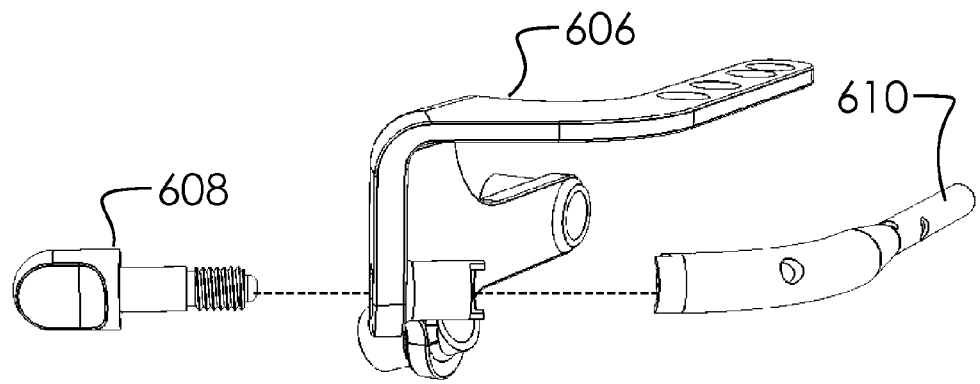
FIGS. 8A and 8B illustrate an exploded perspective front view and overview of said triangular screw guide, said thumb screw and said first nail.
Figure 8B:
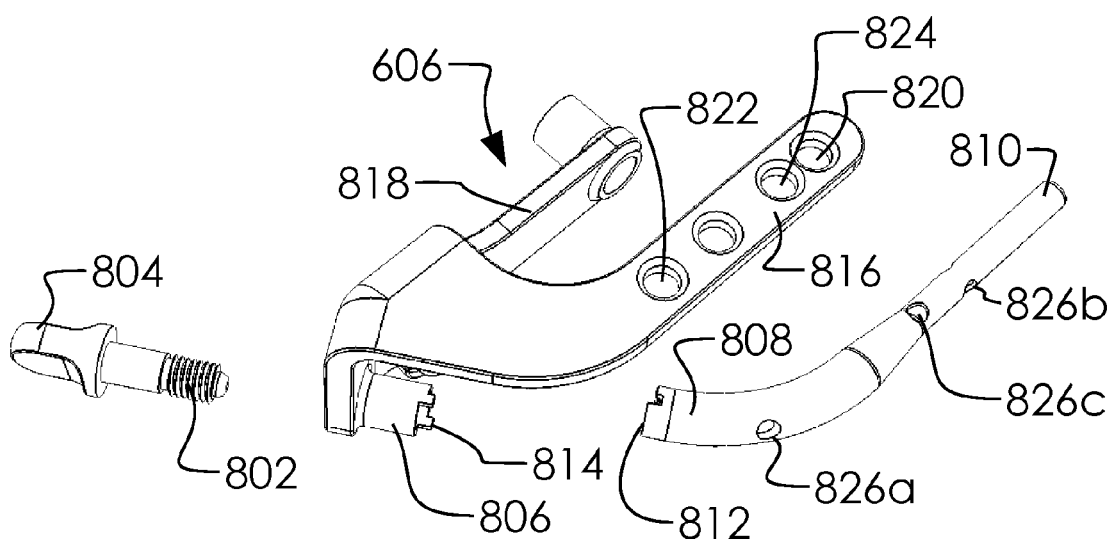

FIGS. 8A and 8B illustrate an exploded perspective front view and overview of said triangular screw guide 606, said thumb screw 608 and said first nail 610. In one embodiment, said thumb screw 608 can comprise a threaded portion 802 and a gripping portion 804. In one embodiment, said triangular screw guide 606 can comprise a thumb screw socket 806. In one embodiment, said first nail 610 can comprise a first end 808 and a second end 810. In one embodiment, said first end 808 can comprise a first coupler 812 and said thumb screw socket 806 can comprise a second coupler 814.

In one embodiment, attaching said first nail 610 to said triangular screw guide 606 can comprise: aligning said threaded portion 802 with said thumb screw socket 806, attaching said first coupler 812 to said second coupler 814, inserting said threaded portion 802 through said thumb screw socket 806 and into said first coupler 812, screwing said threaded portion 802 into said first coupler 812, and tightening said threaded portion 802 of said thumb screw 608 until said triangular screw guide 606 is firmly held between said thumb screw 608 and said first nail 610.

In one embodiment, said triangular screw guide 606 can comprise a top portion 816 and a side portion 818. In one embodiment, said side portion 818 can comprise a plurality of top apertures. In one embodiment, said plurality of top apertures can comprise a first aperture 820, a second aperture 822 and a third aperture 824.

In one embodiment, said first nail 610 can comprise a plurality of threaded female apertures each capable of receiving a portion of said threaded portions of said one of said plurality of screws. In one embodiment, said plurality of threaded female apertures can comprise a first female aperture 826a, a second female aperture 826b and a third female aperture 826c.

Figure 9:
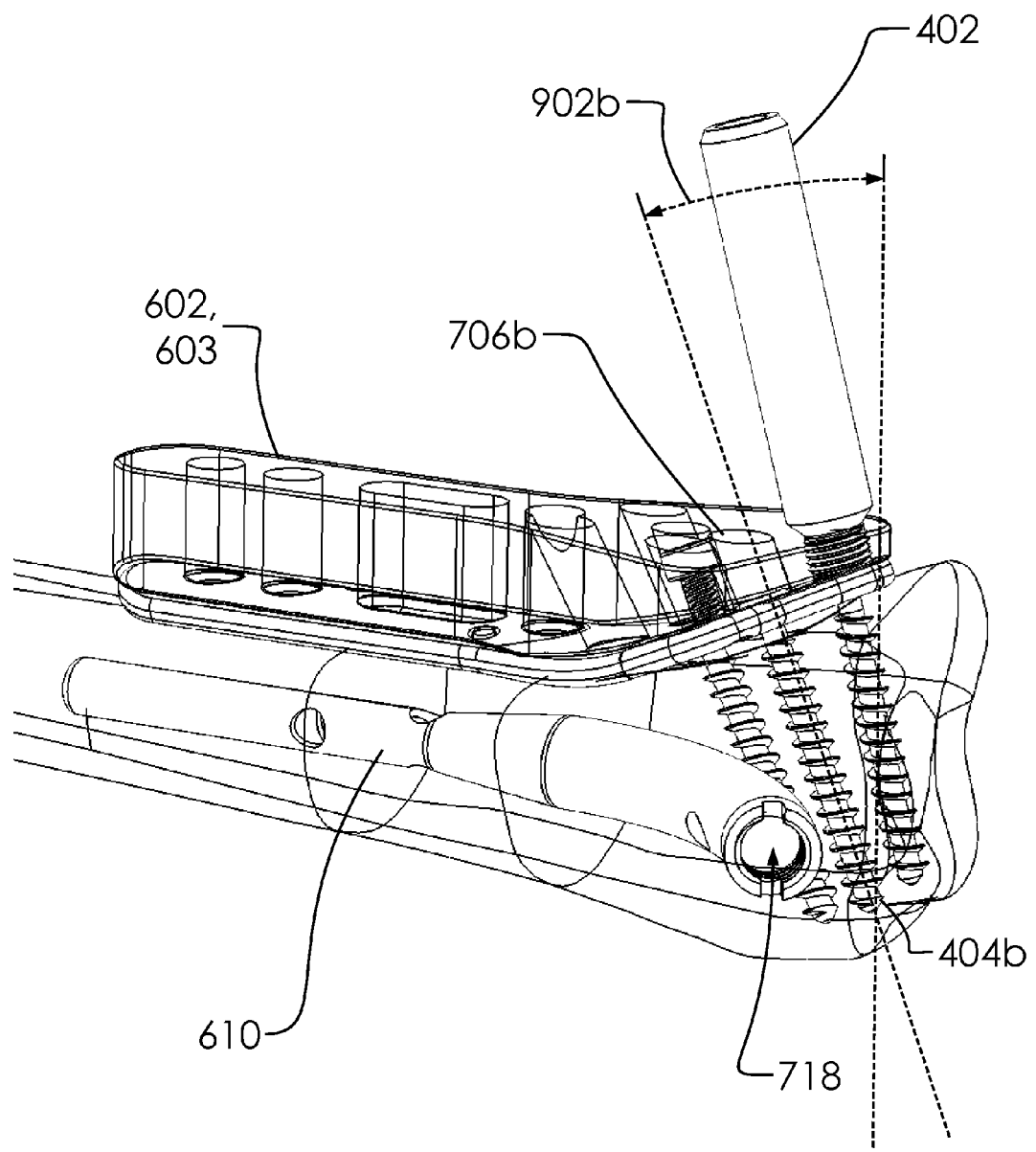
FIG. 9 illustrates a wireframe perspective overview said first nail inserted into said first bone.

FIG. 9 illustrates a wireframe perspective overview said first nail 610 inserted into said first bone 100. In one embodiment, inserting said first nail 610 into said first bone 100 can comprise: drilling a portal at said entry point 718, inserting a portion of said first nail 610 into a medullary cavity of said first bone 100.

In one embodiment, said plurality of channels of said aiming assembly 603 (here, said channeling assembly 604) are capable of directing said plurality of screws through said first fixation plate 102 and into said first bone 100 at a set of predetermined entry angles. For example, in one embodiment, said second channel 706b can direct said second screw 404b into said first bone 100 at a second entry angle 902b.

Figure 10A:
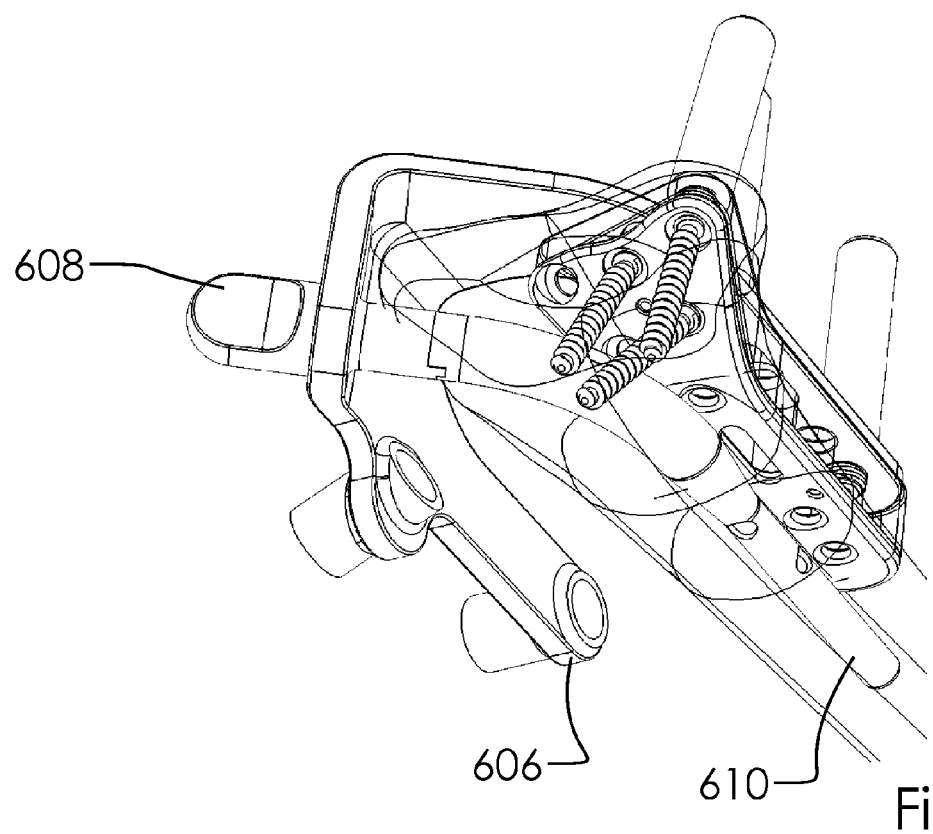
FIGS. 10A and 10B illustrate a perspective lower view and overview of said triangular screw guide, said thumb screw and said first nail attached to one another with said first bone and channeling assembly in a wireframe view.
Figure 10B:
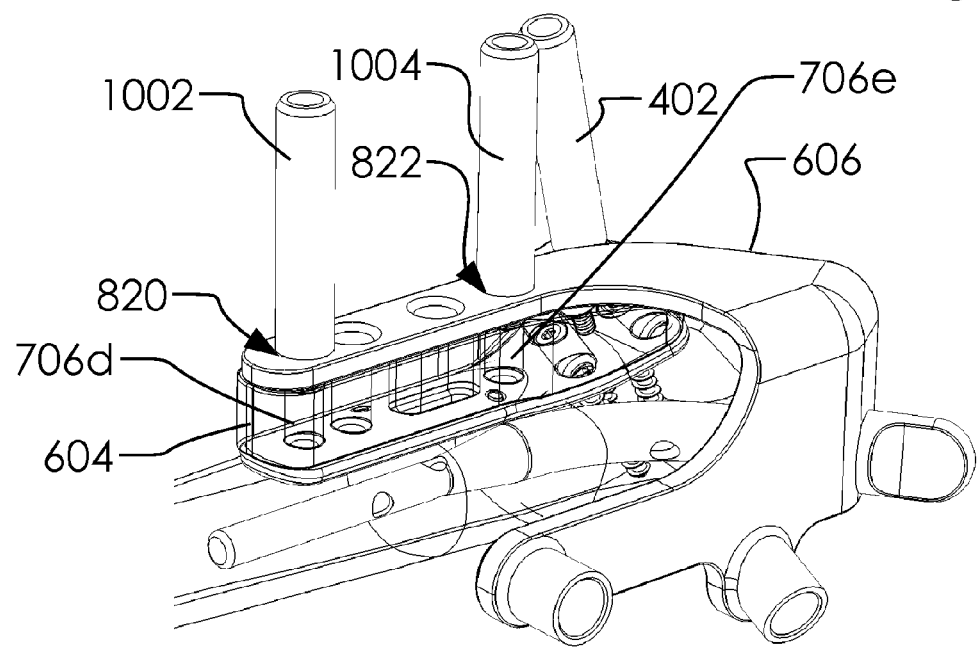

FIGS. 10A and 10B illustrate a perspective lower view and overview of said triangular screw guide 606, said thumb screw 608 and said first nail 610 attached to one another with said first bone 100 and channeling assembly 604 in a wireframe view. In one embodiment, said plurality of said drill guide 402 can comprise a first drill guide 1002 and a second drill guide 1004. In one embodiment, aligning said triangular screw guide 606 with said channeling assembly 604 can comprise: aligning said first aperture 820 of said triangular screw guide 606 with said fourth channel 706d, aligning said second aperture 822 with said fifth channel 706e, inserting and attaching said first drill guide 1002 through said first aperture 820 and into fourth channel 706d, and said second drill guide 1004 through said second aperture 822 and into said fifth channel 706e.

In one embodiment, attaching said triangular screw guide 606 to said channeling assembly 604 and said first nail 610 can comprise: aligning said triangular screw guide 606 with said channeling assembly 604, attaching said triangular screw guide 606 to said channeling assembly 604 with said first drill guide 1002 and said second drill guide 1004, insert said thumb screw 608 through said thumb screw socket 806, attaching said thumb screw 608 to said first nail 610, and holding said triangular screw guide 606 between said thumb screw 608 and said first nail 610.

Figure 11A:
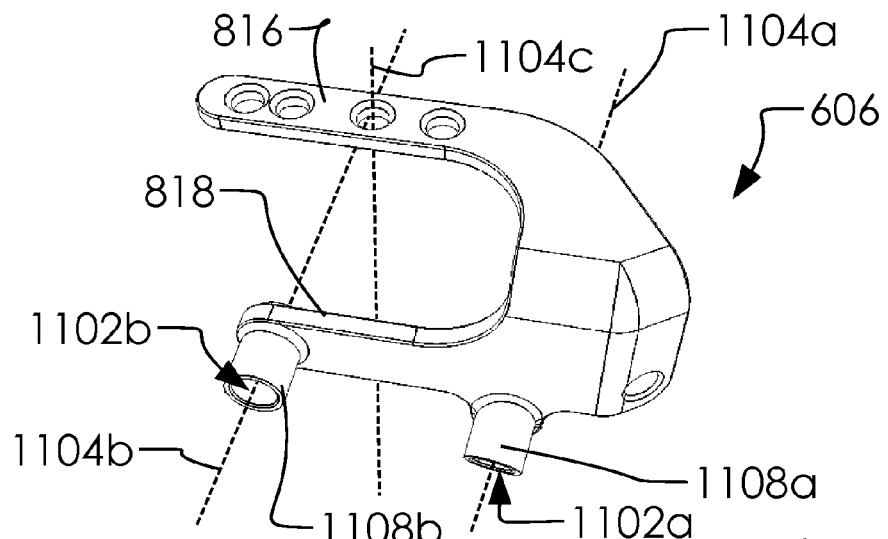
FIGS. 11A and 11B illustrate a perspective overview and a perspective lower view of said triangular screw guide.
Figure 11B:
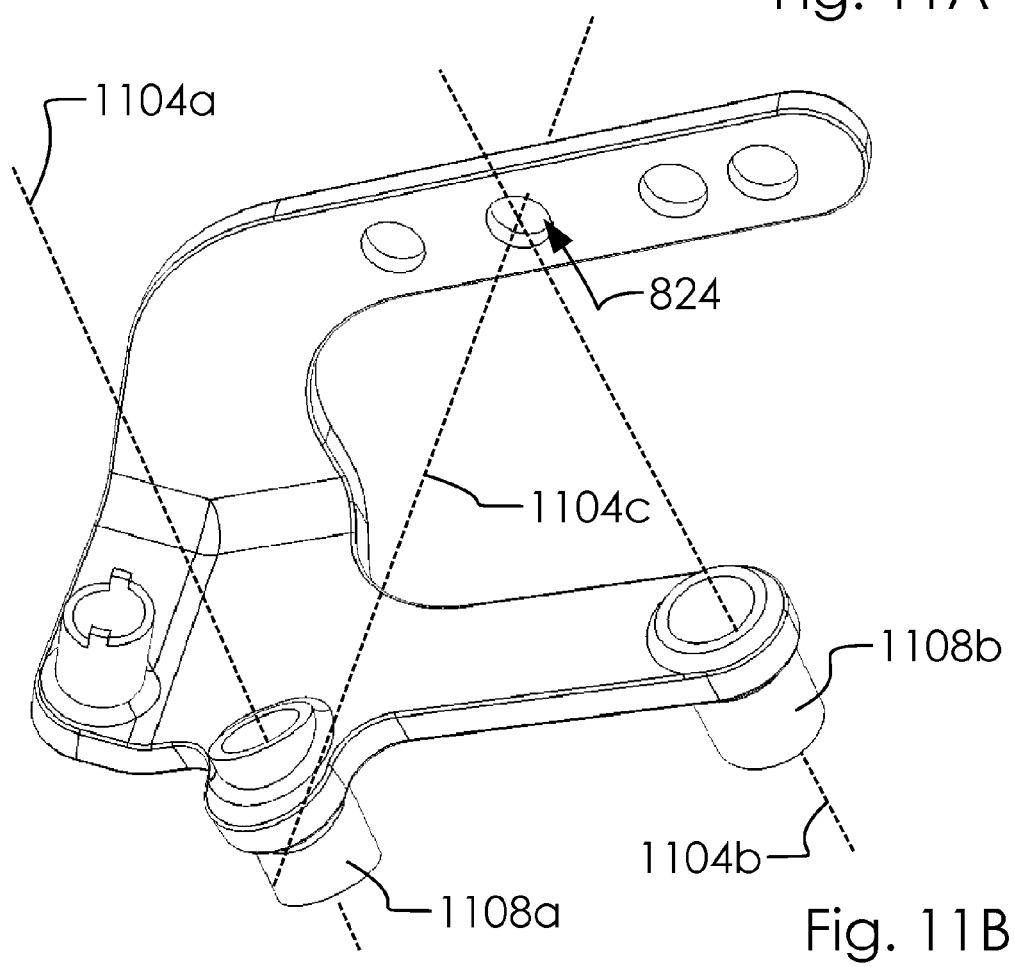

FIGS. 11A and 11B illustrate a perspective overview and a perspective lower view of said triangular screw guide 606. In one embodiment, said triangular screw guide 606 can comprise a plurality of channels capable of aligning a portion of said plurality of screws and/or drilling tools with said plurality of threaded female apertures of said first nail 610.

In one embodiment, said plurality of channels of said triangular screw guide 606 can comprise a first channel 1102a (having a first axis 1104a), a second channel 1102b (having a second axis 1104b) and said third aperture 824 (having a third axis 1104c).

Said side portion 818 of said triangular screw guide 606 can comprise one or more side apertures. In one embodiment, said one or more side apertures can comprise a first aperture 1108a (comprising said first channel 1102a) and a second aperture 1108b (comprising said second channel 1102b).

Figure 12A:
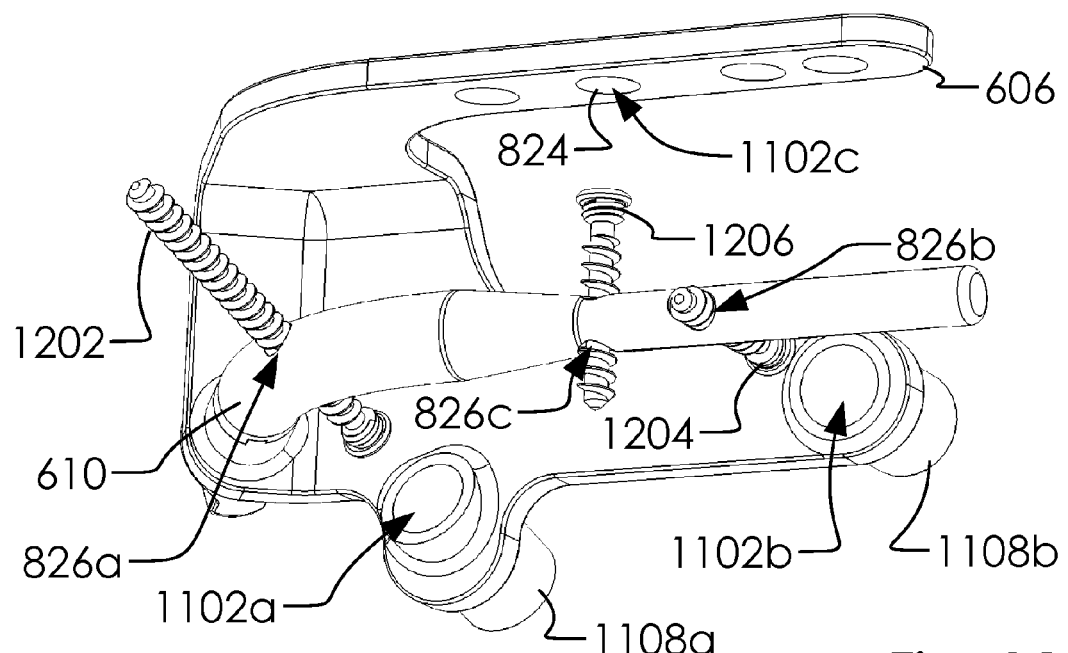
FIGS. 12A and 12B illustrate a perspective side view and a perspective front view of said first nail attached to said triangular screw guide with three of said plurality of screws.
Figure 12B:
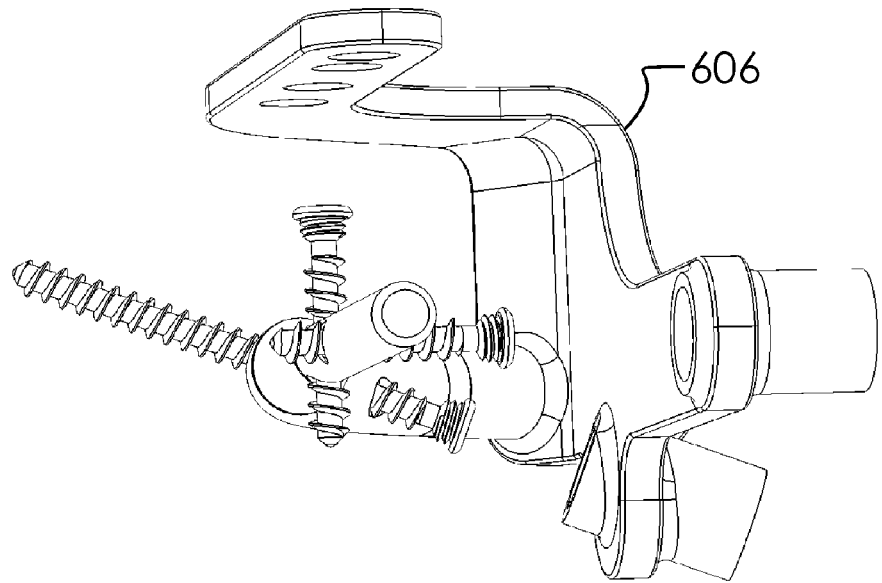

FIGS. 12A and 12B illustrate a perspective side view and a perspective front view of said first nail 610 attached to said triangular screw guide 606 with three of said plurality of screws. In one embodiment, said plurality of screws can comprise an eleventh screw 1202, a twelfth screw 1204 and a thirteenth screw 1206. In one embodiment, said first axis 1104a aligns with said first female aperture 826a, said second axis 1104b aligns with said second female aperture 826b, and said third central axis 1104c aligns with said third female aperture 826c. In one embodiment, attaching said thirteenth screw 1206 can comprise the same screw as said ninth screw 404k.

In one embodiment, a method of using said surgical aiming system 111 can comprise: inserting said first nail 610 into said first bone 100; attaching said triangular screw guide 606 to said first nail 610; aligning and inserting a portion of said plurality of screws with/through said plurality of channels of said triangular screw guide 606; locating said plurality of threaded female apertures with said portion of said plurality of screws, and securing said first fixation plate 102 and said first nail 610 to one another in a relatively fixed position. The benefit of this feature is substantial, as said first nail 610 is inside of said first bone 100, and said first bone 100 is within an arm of a patient; thus, using said plurality of channels to find said plurality of threaded female apertures on said first nail 610 can comprise a useful tool to surgeons.

FIGS. 13A, 13B, 13C, 13D and 13E illustrate a series of perspective overviews of a stacked drilling system 1300. In one embodiment, said stacked drilling system 1300 can comprise a tissue sleeve 1302, a drill sleeve 1304, and a trocar 1306. In one embodiment, said surgical aiming system 111 can comprise a one or more of said stacked drilling system 1300. In one embodiment, each of said stacked drilling system 1300 can slide through said first aperture 1108a and said second aperture 1108b. In one embodiment, attaching plurality of screws through said first aperture 1108a and/or said second aperture 1108b can comprise preparing a plurality of apertures in said first bone 100 for said plurality of screws. In one embodiment, preparing a plurality of apertures in said first bone 100 for said plurality of screws can comprise: inserting said tissue sleeve 1302 into said first aperture 1108a or said second aperture 1108b; pressing and/or drilling said tissue sleeve 1302 through a tissue of said patient's arm; inserting a portion of said drill sleeve 1304 through said tissue sleeve 1302; pressing and/or drilling said drill sleeve 1304 into said arm; inserting a portion of said trocar 1306 through said drill sleeve 1304; pressing and/or drilling said trocar 1306 down to said first bone 100; removing said trocar 1306; drilling through said drill sleeve 1304; removing said drill sleeve 1304 from said tissue sleeve 1302; and screwing said eleventh screw 1202 and/or thirteenth screw 1206 through said tissue sleeve 1302 and into said plurality of threaded female apertures of said first nail 610.

Figure 14A:
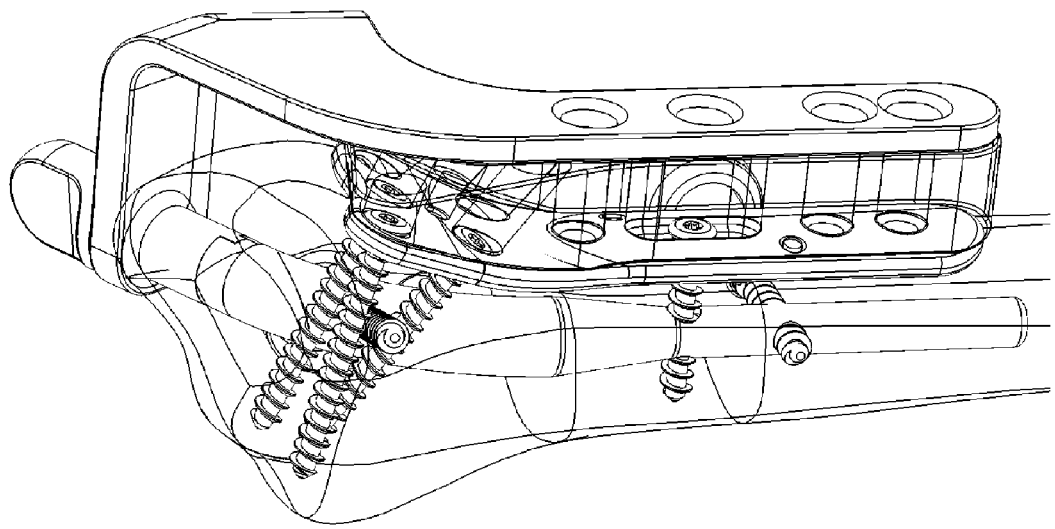
FIGS. 14A and 14B illustrate a wireframe view and a solid view of a perspective overview of said first bone comprising said first nail inserted and attached to said first fixation plate with said channeling assembly, said triangular screw guide, and said thumb screw.
Figure 14B:
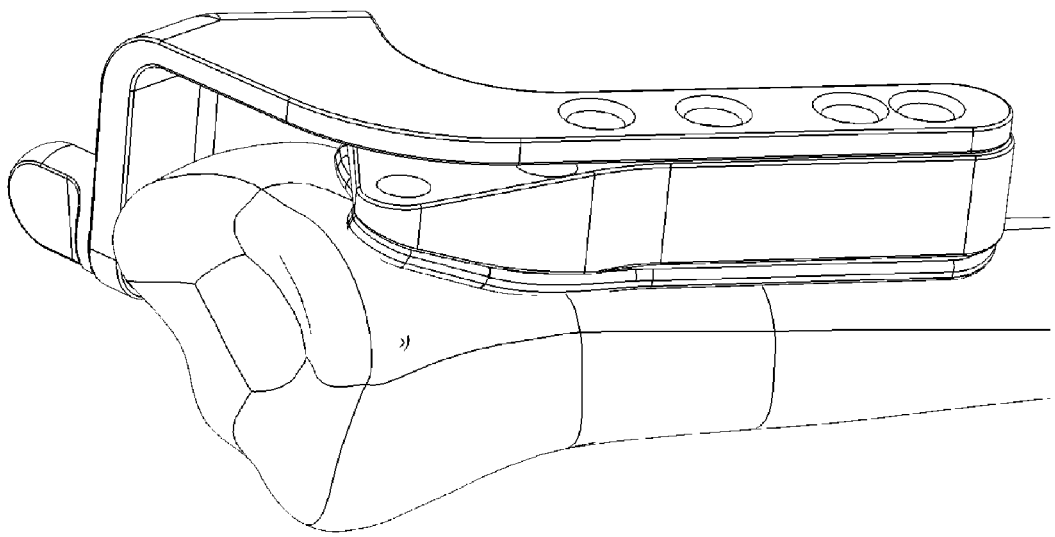

FIGS. 14A and 14B illustrate a wireframe view and a solid view of a perspective overview of said first bone 100 comprising said first nail 610 inserted and attached to said first fixation plate 102 with said channeling assembly 604, said triangular screw guide 606, and said thumb screw 608.

Figure 15:
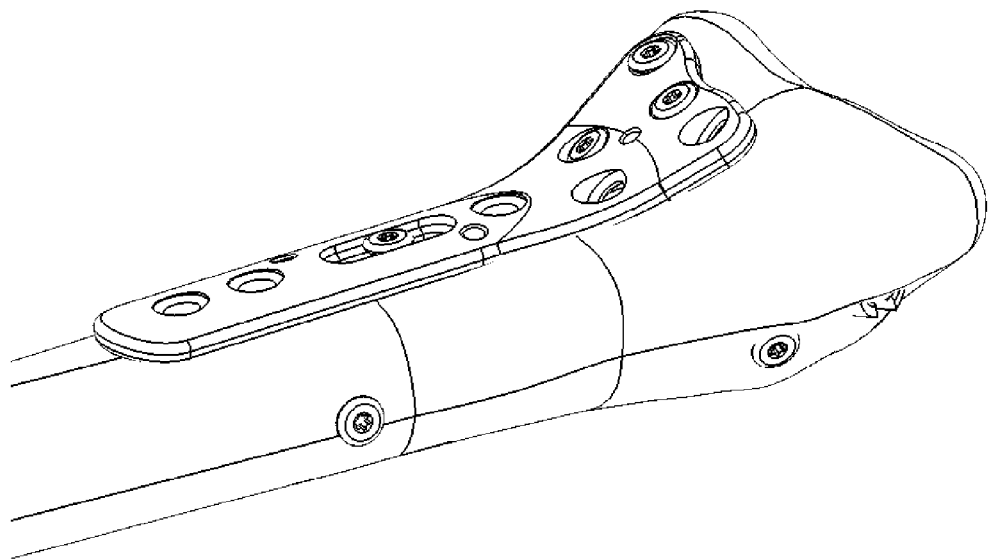
FIG. 15 illustrates a perspective overview of said first bone 100 with said first fixation plate attached, said first nail inserted, and a portion of said plurality of screws installed.

FIG. 15 illustrates a perspective overview of said first bone 100 with said first fixation plate 102 attached, said first nail 610 inserted, and a portion of said plurality of screws installed. In one embodiment, said surgical aiming system 111 can comprise: installing said first fixation plate 102, said first nail 610 and said plurality of screws to holding said surgical aiming system 111 to said first bone 100.

Figure 16A:
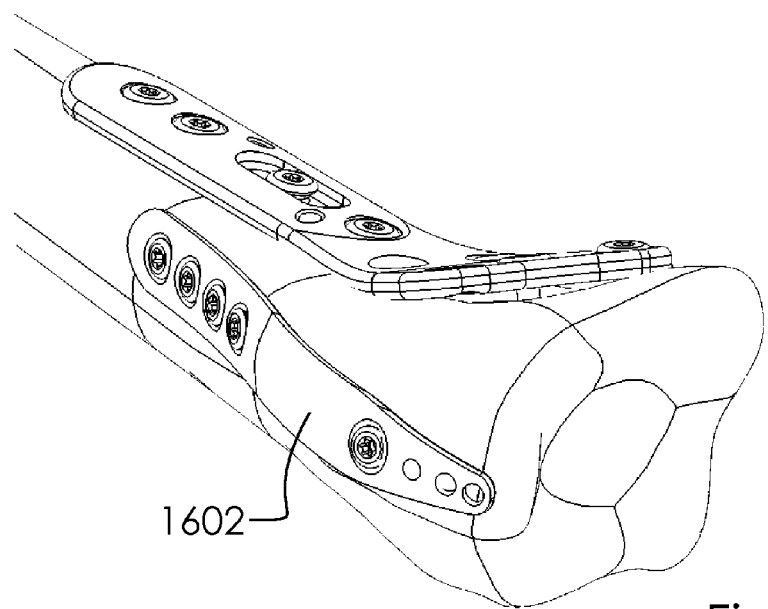
FIGS. 16A, 16B and 16C illustrate a perspective overview said surgical aiming system attached to said first bone with said first fixation plate and a supplementary plate.
Figure 16B:
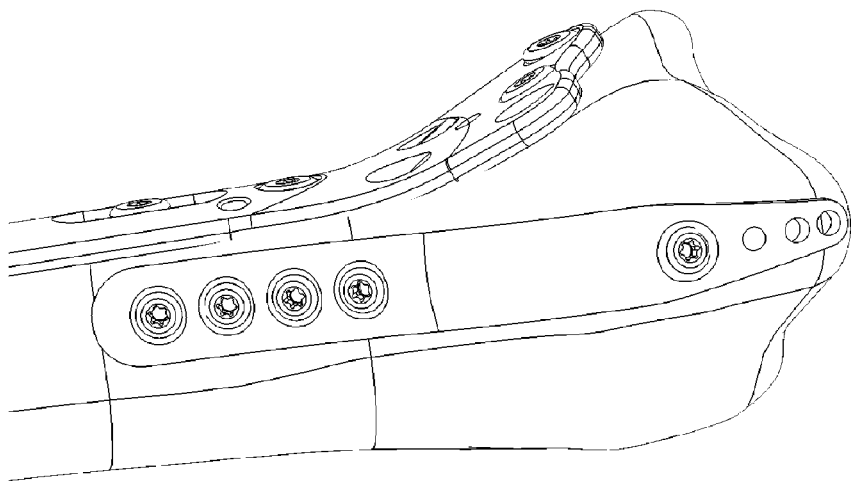
Figure 16C:
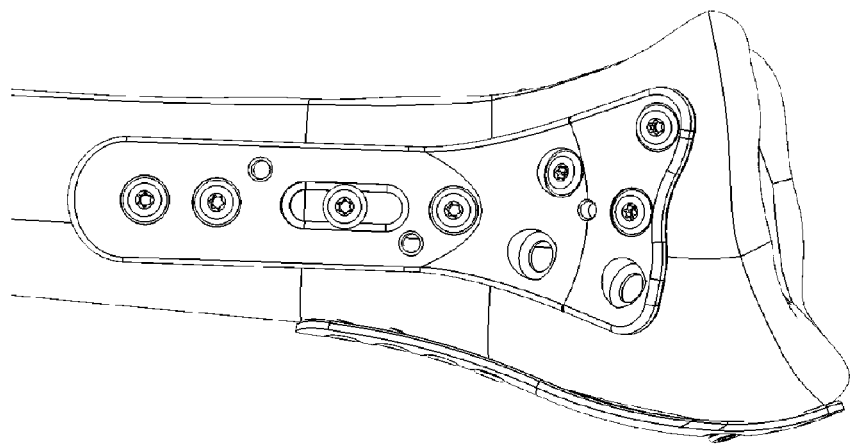
Figure 17A:
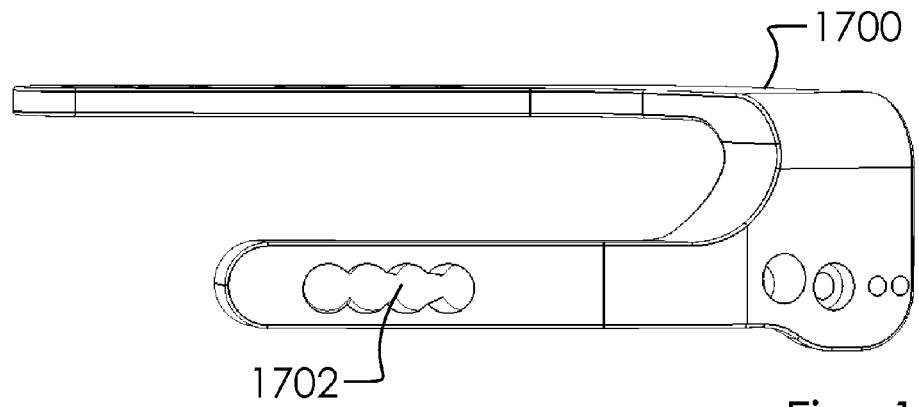
FIGS. 17A, 17B, 17C and 17D illustrate an elevated side view, an elevated top view, an elevated front view and a perspective lower view of a triangular screw guide.
Figure 17B:
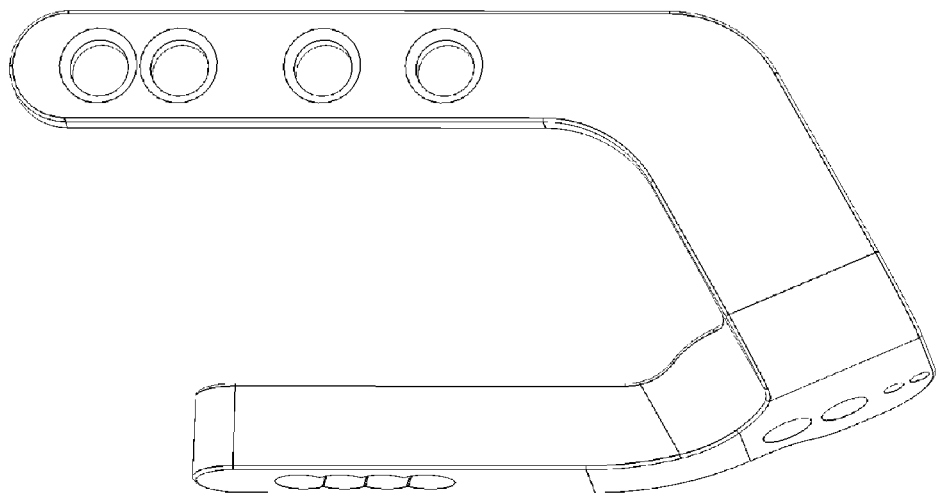
Figure 17C:
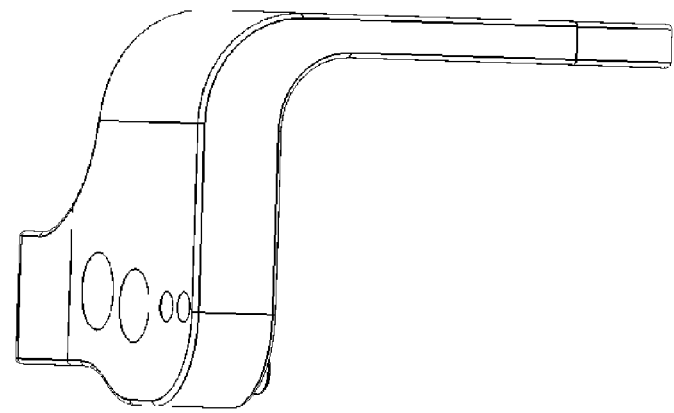
Figure 17D:
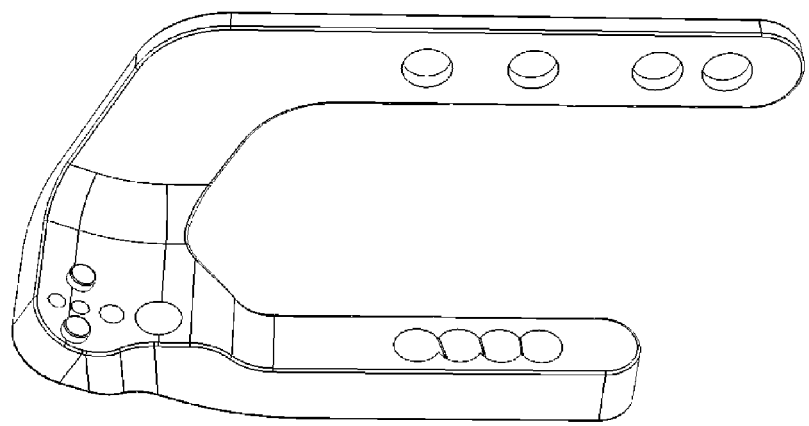

FIGS. 16A, 16B and 16C illustrate a perspective overview said surgical aiming system 111 attached to said first bone 100 with said first fixation plate 102 and a supplementary plate 1602. In one embodiment, said surgical aiming system 111 can comprise a one or more plates attached to said first bone 100. In one embodiment, said one or more plates attached to said first bone 100 can comprise said first fixation plate 102 and a supplementary plate 1602. In one embodiment, said supplementary plate 1602 can support a styloid portion of said first bone 100 while said first fixation plate 102 can support a top portion of said first bone 100. In one embodiment, said supplementary plate 1602 and said first fixation plate 102 can attach around said first bone 100 as illustrated (substantially at a perpendicular angle relative to said first nail 610) or at differing angles relative to said first nail 610. In one embodiment, said supplementary plate 1602 can be useful for reconstructing said first bone 100, where additional support is required in an operation. In one embodiment, said supplementary plate 1602 can comprise one or more apertures capable of receiving one or more of said plurality of screws, as illustrated.

FIGS. 17A, 17B, 17C and 17D illustrate an elevated side view, an elevated top view, an elevated front view and a perspective lower view of a triangular screw guide 1700. In one embodiment, said triangular screw guide 1700 can be substantially identical to said triangular screw guide 606, but-for a rearrangement of said channels, as illustrated. In one embodiment, a multi-channel aperture 1702 can provide for the direction of a one or more screws into said supplementary plate 1602, as illustrated infra.

Figure 18A:
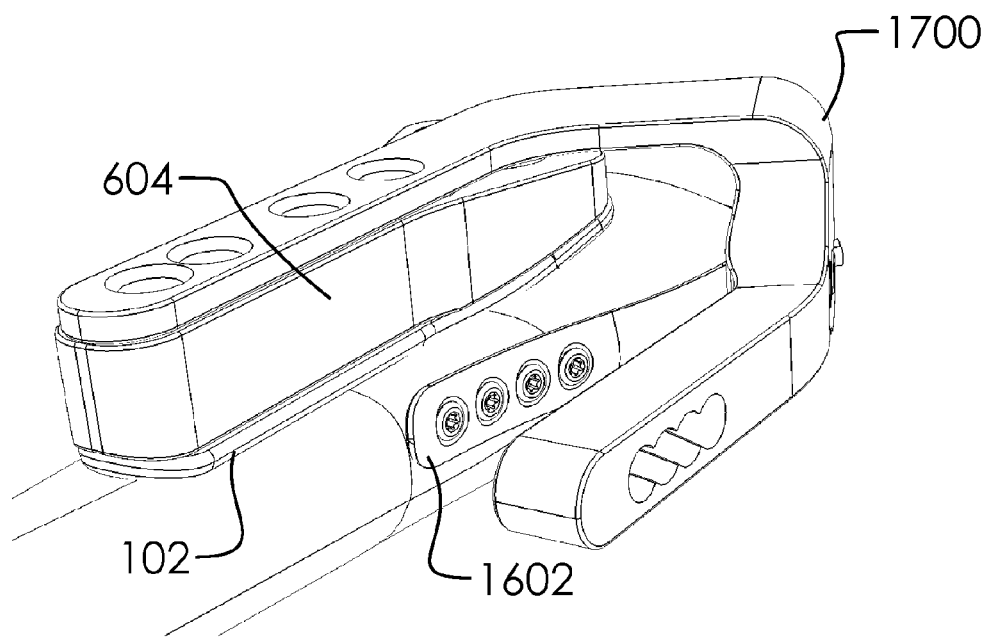
FIGS. 18A and 18B illustrate a series of perspective overviews of said triangular screw guide aligned with said first fixation plate and said supplementary plate.
Figure 18B:
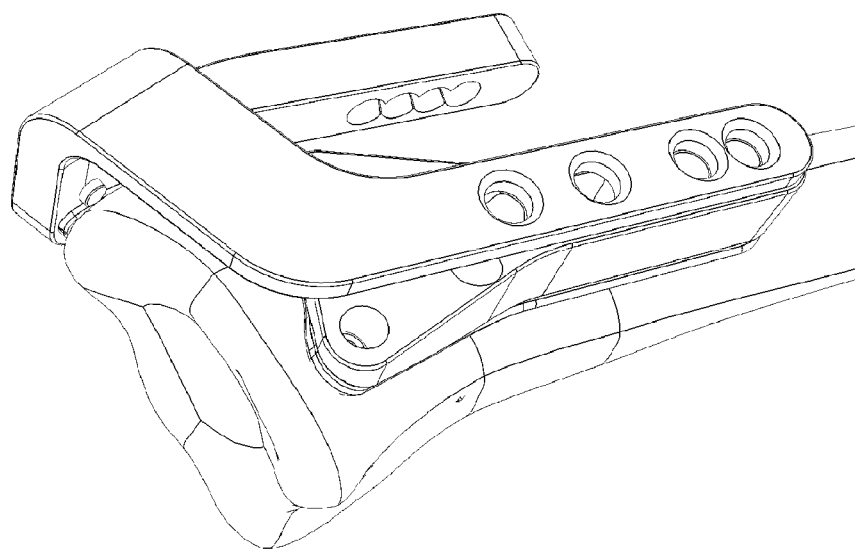

FIGS. 18A and 18B illustrate a series of perspective overviews of said triangular screw guide 1700 aligned with said first fixation plate 102 and said supplementary plate 1602. In one embodiment, said second embodiment of said surgical aiming system 111 can comprise said first fixation plate 102, said supplementary plate 1602, said channeling assembly 604, said triangular screw guide 1700, and said plurality of screws. In one embodiment, attaching said second embodiment of said surgical aiming system 111 can comprise: attaching said first fixation plate 102 to said first bone 100; aligning said supplementary plate 1602 with said styloid portion of said first bone 100; aligning said channeling assembly 604 and said triangular screw guide 1700 with said first fixation plate 102; attaching said supplementary plate 1602 to said first fixation plate 102.

Figure 19A:
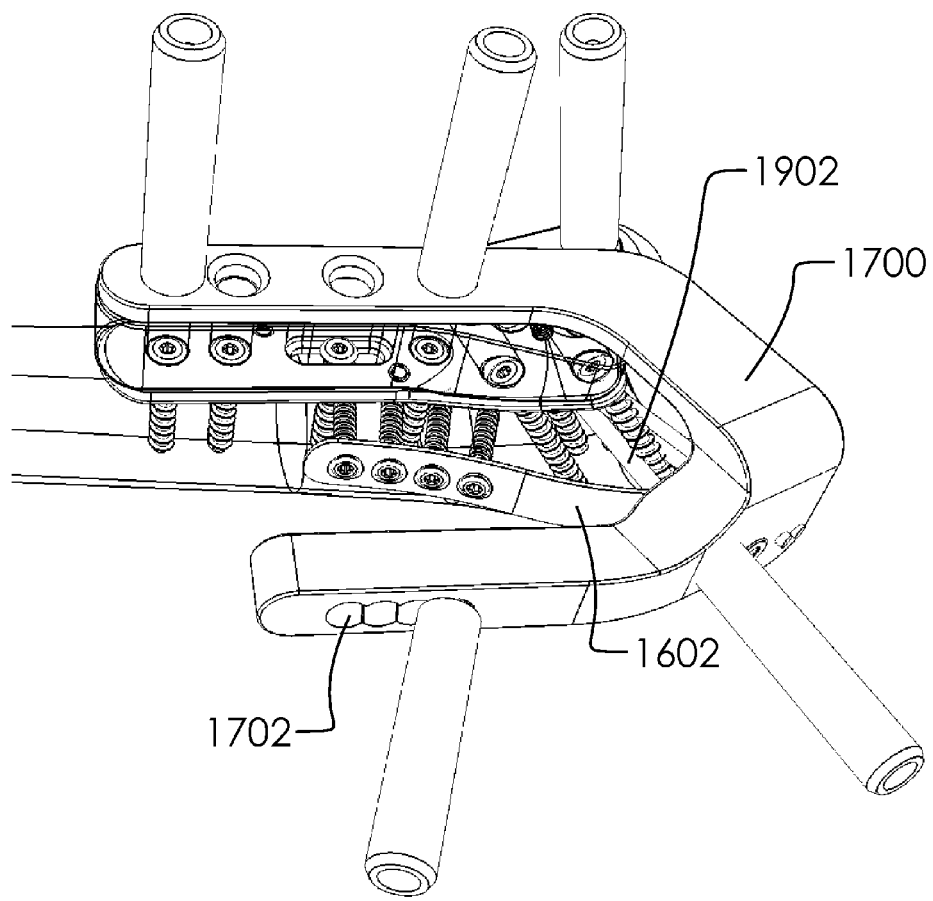
FIGS. 19A and 19B illustrate a perspective wireframe overview and detailed view of said triangular screw guide, supplementary plate, a one or more nails, and said first fixation plate attached to said first bone.
Figure 19B:
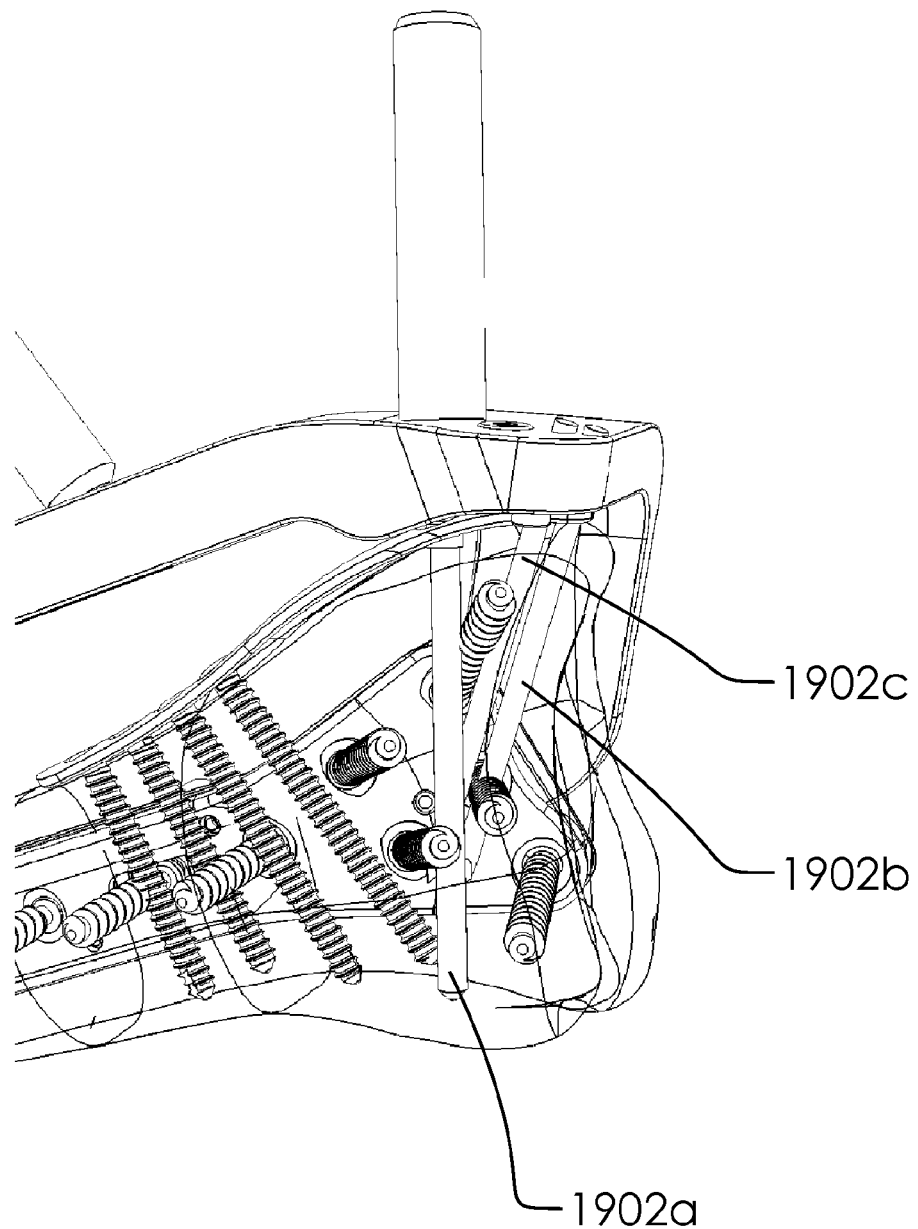

FIGS. 19A and 19B illustrate a perspective wireframe overview and detailed view of said triangular screw guide 1700, supplementary plate 1602, a one or more nails, and said first fixation plate 102 attached to said first bone 100. In one embodiment, said triangular screw guide 1700 can be used to insert said one or more nails (comprising a first nail 1902a, a second nail 1902b and a third nail 1902c) into said first bone 100.

Figure 20A:
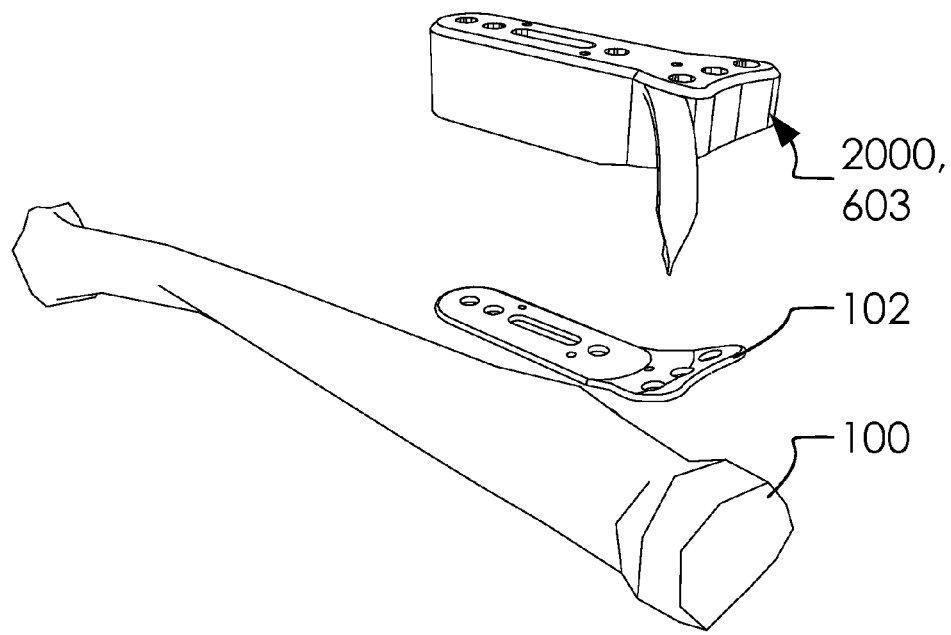
FIGS. 20A and 20B illustrate a perspective overview of a first aiming assembly, said first fixation plate and said first bone.
Figure 20B:
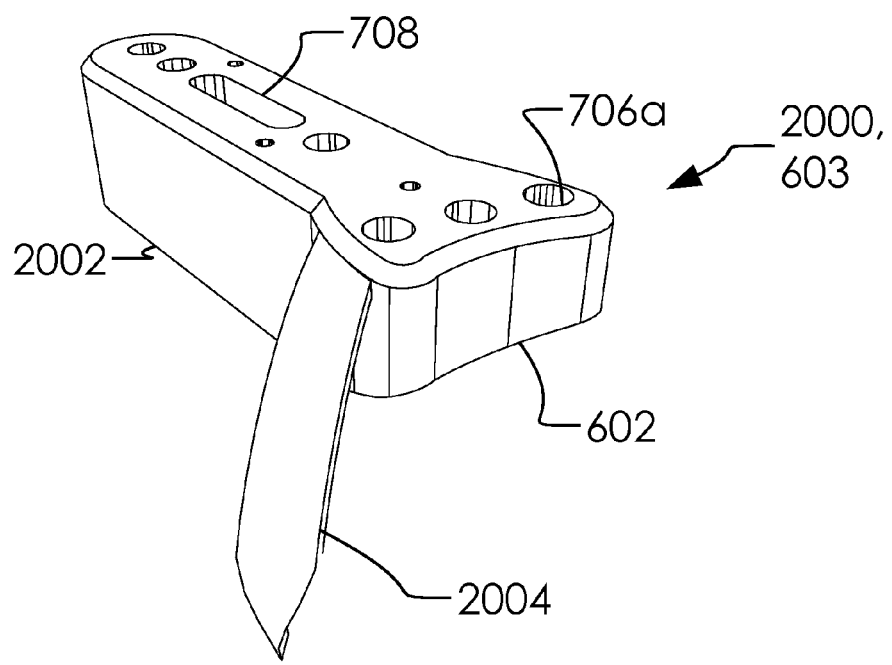

FIGS. 20A and 20B illustrate a perspective overview of a first aiming assembly 2000, said first fixation plate 102 and a first bone 100. In one embodiment, said first aiming assembly 2000 can comprise an integrated component comprising parts previously introduced as said channeling assembly 604 and said intramedullary entry locator 602. In one embodiment, said first aiming assembly 2000 can comprise said aiming assembly 603 in one fully integrated part.

Accordingly, said surgical aiming system 111 can comprise: a one or more fixation plates (such as said first fixation plate 102) capable of attaching extramedullary to said first bone 100, said aiming assembly 603 (such as said first aiming assembly 2000) capable of attaching intramedullary to sad first bone 100, and a plurality of screws to attach them to one another; wherein, said surgical aiming system 111 is capable of holding said extramedullary and intramedullary components in a relatively fixed position to one another during assembly of said surgical aiming system 111.

In one embodiment, said surgical aiming system (such as said first aiming assembly 2000) can comprise a one-piece component.

In one embodiment, said first aiming assembly 2000 can comprise a spacing portion 2002, a pointing device 2004, and a plurality of channels (such as said first channel 706a and said central channel 708). In one embodiment, said first aiming assembly 2000 can be used in conjunction with a one or more fixation plates (such as said first fixation plate 102).

Figure 21A:
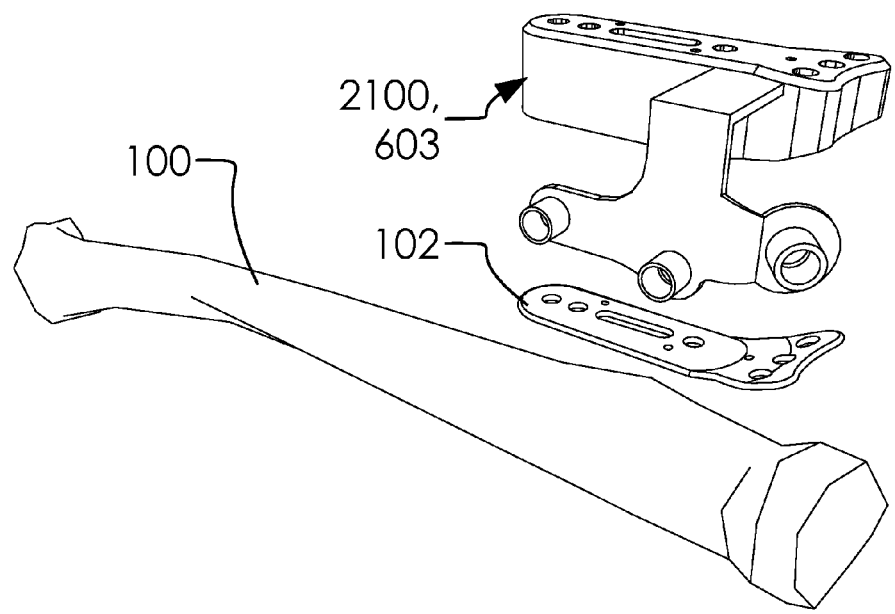
FIGS. 21A and 21B illustrate a perspective overview of a second aiming assembly, said first bone and said first fixation plate.
Figure 21B:
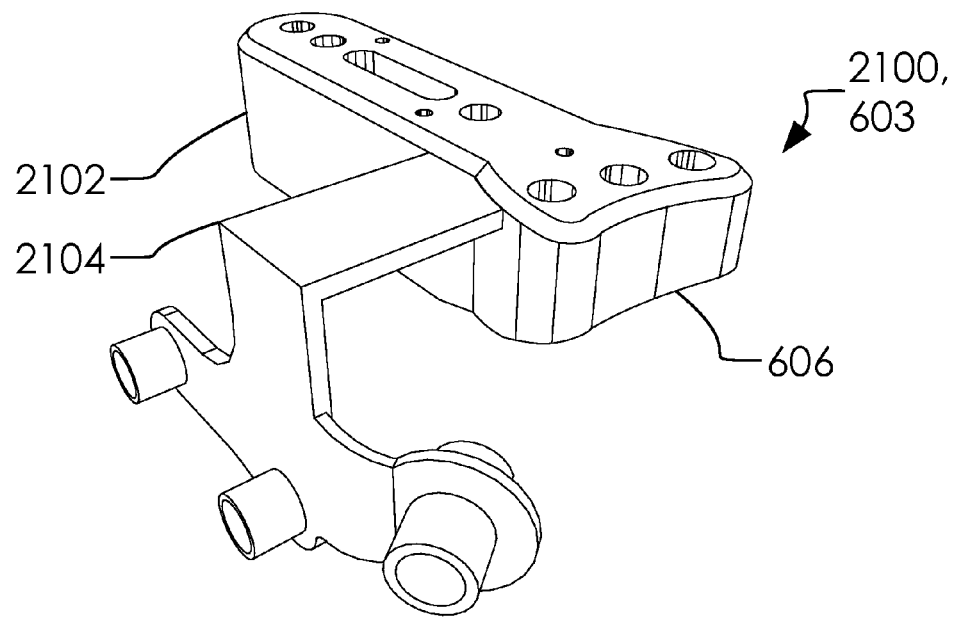

FIGS. 21A and 21B illustrate a perspective overview of a second aiming assembly 2100, said first bone 100 and said first fixation plate 102. In one embodiment, said second aiming assembly 2100 can be similar to said first aiming assembly 2000, in that it is an integral component used in lieu of a plurality of components as illustrated with said channeling assembly 604 and said triangular screw guide 606. In one embodiment, said second aiming assembly 2100 can comprise one of said aiming assembly 603, as discussed for said first aiming assembly 2000, supra. In one embodiment, said second aiming assembly 2100 can comprise a spacing portion 2102 and a triangular screw guide portion 2104.

In one embodiment, holding said extramedullary and intramedullary components said surgical aiming system 111 in a relatively fixed position to one another can comprise: attaching said one or more fixation plates (such as said first fixation plate 102) extramedullary to said first bone 100; attaching said aiming assembly 603 (such as said second aiming assembly 2100) intramedullary to sad first bone 100 via a plurality of screws.

Figure 22A:
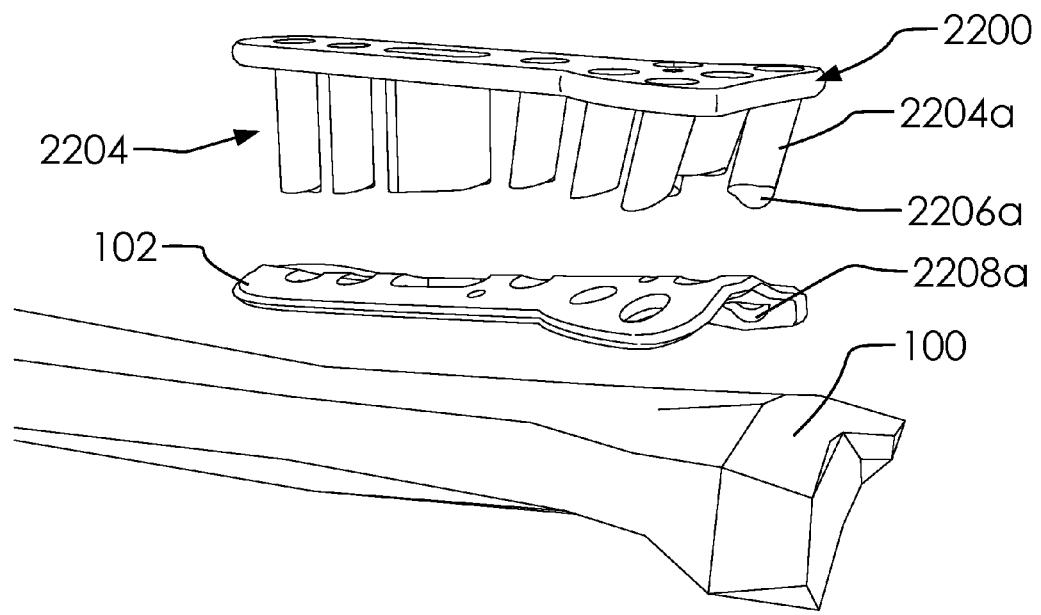
FIGS. 22A and 22B illustrate a perspective overview of a first channeling assembly, said first fixation plate and said first bone.
Figure 22B:
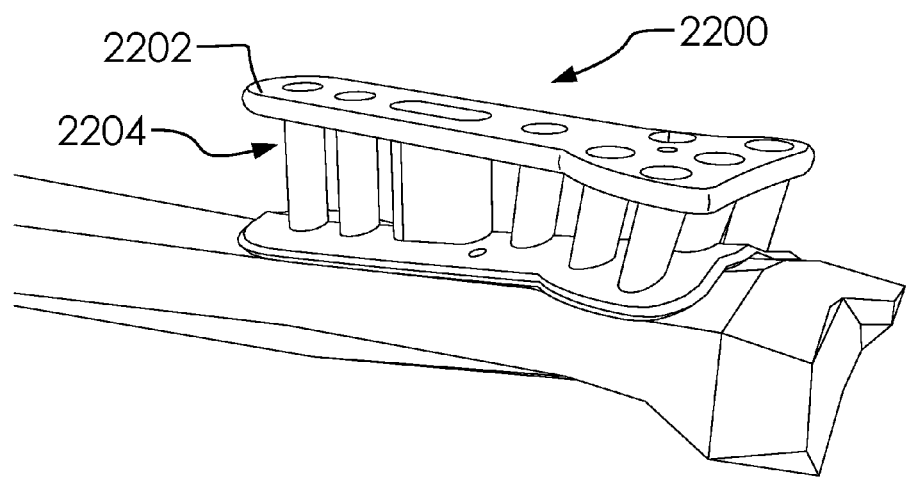

FIGS. 22A and 22B illustrate a perspective overview of a channeling assembly 2200, said first bone 100 and said first fixation plate 102. In one embodiment, said channeling assembly 2200 can be similar to said channeling assembly 604 in that excess material between a one or more channels is absent. In one embodiment, said channeling assembly 2200 can be used in lieu of said channeling assembly 604 while saving on materials cost and weight.

In one embodiment, said channeling assembly 2200 can comprise a frame 2202 and a plurality of channels 2204 (such as a first channel 2204a). In one embodiment, said plurality of channels are capable of mating with said first fixation plate 102. For example, in one embodiment, said first channel 2204a (having a lower portion 2206a) can align with a first aperture 2208a in said first fixation plate 102. In one embodiment, said channeling assembly 2200 can be used with a one or more fixation plates or a one or more aiming assemblies.

Likewise, in one embodiment, said pointing device 2004 and/or said triangular screw guide portion 2104 can be attached to said channeling assembly 2200. Thus, said channeling assembly 2200 is included as an exemplary embodiment for said channeling assembly 604 and illustrates that a solid block need not be employed to provide the benefits of said channeling assembly 604 and the overall benefits of said surgical aiming system 111.

Various changes in the details of the illustrated operational methods are possible without departing from the scope of the following claims. Some embodiments may combine the activities described herein as being separate steps. Similarly, one or more of the described steps may be omitted, depending upon the specific operational environment the method is being implemented in. It is to be understood that the above description is intended to be illustrative, and not restrictive. For example, the above-described embodiments may be used in combination with each other or in another anatomic location with appropriately configured hardware and guides. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

The invention claimed is:

1. A surgical aiming system comprising:
   a one or more fixation plates, an aiming assembly, a one or more nails and a plurality of screws;
   said one or more fixation plates comprising a first fixation plate;
   said aiming assembly comprising a channeling assembly and a plurality of channels;
   said one or more fixation plates comprising a plurality of plate apertures capable of receiving a portion of said plurality of screws;
   said plurality of channels in said aiming assembly are capable of aligning a portion of said plurality of screws with said plurality of plate apertures in said first fixation plate;
   said first fixation plate having
      a first end,
      a second end,
      a top surface, and
      a bottom surface;
   said plurality of plate apertures comprising a first plate aperture and a second first plate aperture;
   said channeling assembly having
      a thickness,
      a top surface, and a bottom surface;
said bottom surface of said first fixation plate substantially configured to couple with a surface of a first bone of a skeletal system;
said bottom surface of said aiming assembly substantially couples with said top surface of said first fixation plate;
said plurality of channels receive and align said plurality of screws as said plurality of screws are inserted through said plurality of plate apertures and configured to be secured to said first bone;
said first fixation plate being extramedullary attached to a portion of said surface of said first bone;
said plurality of channels of said aiming assembly being aligned to identify a one or more intramedullary locations including
an entry point for said one or more nails, and
an alignment and entry point for each among said plurality of plate apertures;
said aiming assembly comprising an assembly of a plurality of components;
said aiming assembly comprising a channeling assembly and an intramedullary entry locator having a pointing device;
said one or more nails comprising a first nail;
said intramedullary entry locator having an upper portion and a lower portion;
said upper portion comprising a first channel and a second channel of said intramedullary entry locator;
said lower portion comprising said pointing device;
said upper portion being capable of releasably attaching to said channeling assembly of said aiming assembly;
said upper portion being substantially parallel with said channeling assembly of said aiming assembly when attached thereto; and
said lower portion bending down and away from said upper portion until said pointing device is substantially perpendicular to said upper portion.

2. A surgical aiming system comprising: a one or more fixation plates, an aiming assembly, a one or more nails and a plurality of screws; said one or more fixation plates comprising a first fixation plate; said aiming assembly comprising a channeling assembly and a plurality of channels; said one or more fixation plates comprising a plurality of plate apertures capable of receiving a portion of said plurality of screws; said plurality of channels in said aiming assembly are capable of aligning a portion of said plurality of screws with said plurality of plate apertures in said first fixation plate; said first fixation plate having a first end, a second end, a top surface, and a bottom surface; said plurality of plate apertures comprising a first plate aperture and a second first plate aperture; said channeling assembly having a thickness, a top surface, and a bottom surface; said bottom surface of said first fixation plate substantially configured to couple with a surface of a first bone of a skeletal system; said bottom surface said aiming assembly substantially couples with said top surface of said first fixation plate; said plurality of channels receive and align said plurality of screws as said plurality of screws are inserted through said plurality of plate apertures and configured to be secured to said first bone; said first fixation plate being extramedullary attached to a portion of said surface of said first bone; and said plurality of channels of said aiming assembly being aligned to identify a one or more intramedullary locations including an entry point for said one or more nails, and an alignment and entry point for each among said plurality of plate apertures, wherein said aiming assembly comprising an assembly of a plurality of components; and said aiming assembly comprising a channeling assembly and an intramedullary entry locator having a pointing device, wherein said one or more nails comprising a first nail; said intramedullary entry locator having an upper portion and a lower portion; said upper portion comprising a first channel and a second channel of said intramedullary entry locator; said lower portion comprising said pointing device; and said upper portion being capable of releasably attaching to said channeling assembly of said aiming assembly, wherein said first nail comprising a plurality of threaded female apertures; said aiming assembly comprising a triangular screw guide;
said triangular screw guide comprising a plurality of channels; said triangular screw guide is capable of releasably attaching to said first nail; with said triangular screw guide attached to said first nail, said plurality of channels in said triangular screw guide are aligned with said plurality of threaded female apertures of said first nail; and aligning a portion of said plurality of screws with said plurality of threaded female apertures comprises attaching said portion of said plurality of screws into said first bone through said plurality of channels of said triangular screw guide.

3. The surgical aiming system of claim 2 wherein:
said aiming assembly comprising a one-piece component.

4. The surgical aiming system of claim 2 wherein:
said upper portion being substantially parallel with said channeling assembly of said aiming assembly when attached thereto; and
said lower portion bending down and away from said upper portion until said pointing device is substantially perpendicular to said upper portion.

5. The surgical aiming system of claim 2 wherein:
said pointing device identifying said entry point for said first nail or drill when said upper portion is attached to said channeling assembly; and
said entry point aligned so that said first nail can enter said first bone without hitting said plurality of screws within said first bone.

6. The surgical aiming system of claim 2 wherein:
said first bone of said skeletal system belongs to a mammal.

7. The surgical aiming system of claim 2 wherein:
said first bone of said skeletal system belongs to a human.

8. The surgical aiming system of claim 2 further comprising:
said one or more plates comprising of said first fixation plate a supplementary plate;
said one or more plates attach around a portion of said first bone;
said one or more plates each comprise a portion of said plurality of plate apertures;
said aiming assembly releasably attaches to said one or more plates;
said plurality of channels in said aiming assembly align and direct said plurality of screws into and through said plurality of plate apertures in said one or more plates; and
said one or more plates hold a portion of said first bone from a plurality of surface locations around said one or more nails within said first bone.

9. The surgical aiming system of claim 2 wherein:
said alignment and entry points of said plurality of screws through said plurality of channels of said aiming assembly are predetermined to
avoid intersecting with said one or more nails or
to attach to a portion of said one or more nails.

* * * * *